US008247207B2

(12) United States Patent
Kemble et al.

(10) Patent No.: US 8,247,207 B2
(45) Date of Patent: Aug. 21, 2012

(54) REFRIGERATOR-TEMPERATURE STABLE INFLUENZA VACCINE COMPOSITIONS

(75) Inventors: George Kemble, Fremont, CA (US); George Trager, San Francisco, CA (US); Richard Schwartz, Bethesda, MD (US)

(73) Assignee: Medimmune, LLC, Gaithersburg, MD (US)

(*) Notice: Subject to any disclaimer, the term of this patent is extended or adjusted under 35 U.S.C. 154(b) by 0 days.

(21) Appl. No.: 12/487,343

(22) Filed: Jun. 18, 2009

(65) Prior Publication Data
US 2009/0317425 A1 Dec. 24, 2009

Related U.S. Application Data

(63) Continuation of application No. 11/242,018, filed on Oct. 4, 2005, now abandoned, which is a continuation-in-part of application No. 10/788,236, filed on Feb. 25, 2004, now Pat. No. 7,262,045.

(60) Provisional application No. 60/616,711, filed on Oct. 6, 2004, provisional application No. 60/450,181, filed on Feb. 25, 2003.

(51) Int. Cl.
C12N 7/02 (2006.01)
A61K 39/145 (2006.01)

(52) U.S. Cl. ..................... 435/239; 424/209.1

(58) Field of Classification Search ............... None
See application file for complete search history.

(56) References Cited

U.S. PATENT DOCUMENTS

| | | | |
|---|---|---|---|
| 3,874,999 | A | 4/1975 | Zaremba et al. |
| 4,000,257 | A | 12/1976 | Cano |
| 4,057,626 | A * | 11/1977 | Metzgar et al. ............ 424/209.1 |
| 4,158,054 | A * | 6/1979 | Furminger et al. ......... 424/209.1 |
| 4,337,242 | A * | 6/1982 | Markus et al. ............ 424/202.1 |
| 4,338,296 | A | 7/1982 | Lobmann |
| 4,338,335 | A | 7/1982 | McAleer et al. |
| 4,500,512 | A | 2/1985 | Barme |
| 4,512,285 | A | 4/1985 | McGehee |
| 4,512,972 | A | 4/1985 | Schmidt-Ruppin |
| 5,948,410 | A * | 9/1999 | Van Scharrenburg et al. ............ 424/210.1 |
| 6,039,958 | A | 3/2000 | Koyama |
| 6,146,873 | A | 11/2000 | Kistner et al. |
| 6,177,082 | B1 * | 1/2001 | Dowling et al. ........... 424/209.1 |
| 6,344,354 | B1 | 2/2002 | Webster |
| 6,656,720 | B2 | 12/2003 | Groner et al. |
| 7,262,045 | B2 | 8/2007 | Schwartz et al. |
| 7,344,722 | B1 * | 3/2008 | Maassab et al. .......... 424/206.1 |
| 2003/0108859 | A1 * | 6/2003 | Kistner et al. ................ 435/5 |
| 2004/0029251 | A1 | 2/2004 | Hoffman et al. |
| 2005/0158342 | A1 | 7/2005 | Kemble |
| 2005/0186563 | A1 | 8/2005 | Hoffmann |
| 2006/0110406 | A1 * | 5/2006 | Kemble et al. ........... 424/209.1 |
| 2007/0161085 | A1 | 7/2007 | Trager et al. |
| 2007/0172929 | A1 | 7/2007 | Maassab et al. |
| 2009/0246225 | A1 | 10/2009 | Trager |

FOREIGN PATENT DOCUMENTS

| | | |
|---|---|---|
| CA | 2482946 | 11/2003 |
| EP | 0480949 | 4/1992 |
| EP | 1597400 | 2/2005 |
| GB | 660109 | 10/1951 |
| JP | 6-65096 | 8/1994 |
| JP | 2002-532435 | 2/2002 |
| PI | 0002694 | 2/2002 |
| WO | WO 97/14434 | 4/1997 |
| WO | WO 00/35481 | 6/2000 |
| WO | WO 02/24876 | 3/2001 |
| WO | WO 01/22992 | 4/2001 |
| WO | WO 02/074336 | 9/2002 |
| WO | WO 03/091401 | 11/2003 |
| WO | WO 2004/058156 | 7/2004 |
| WO | WO 2005/014862 | 2/2005 |
| WO | WO 2005/115448 | 12/2005 |
| WO | WO 2006/041819 | 4/2006 |

OTHER PUBLICATIONS

Yannarell et al., Journal of Virological Methods, 2002, 102:15-25.*
ADIS R&D Profile, Drugs R&D, 2003, 4(5):312-319.*
Reimer et al., Science, 1966, 152:1379-1381.*
Alexandrova et al., "Laboratory Properties of Cold-adapted Influenza B Live Vaccine Strains Developed in the US and USSR, and their B/Ann Arbor/1/86 Cold-Adapted Reassortant Vaccine Candidates," Vaccine (1990) 8: 61-64.
"Influenza Virus Vaccine Live Intranasal—MedImmune Vaccines: CAIV-T, Influenza Vaccine Live Intranasal" Drugs R.D. (2003) 4: 312-319.
Arora, D. J., et al. "Concentration and Purification of Influenza Virus from Allantoic Fluid." Anal.Biochem. (1985) 144: 189-92.
Belshe, R. B., et al. "The Efficacy of Live Attenuated, Cold-adapted, Trivalent, Intranasal Influenza virus Vaccine in Children." N.EngU. Med. (1998) 338: 1405-12.
Boyce, T. G., et al. "Safety and Immunogenicity of Adjuvanted and Unadjuvanted Subunit Vaccines Administered Intranasally to Healthy Adults." (2001) 19: 217-26.
Cha, T A., et al "Genotypic Stability of Cold-Adapted Influenza Virus Vaccine in an Efficacy Clinical Trial" 1.Clin.MicrobioL (2000) 38: 839-45.
Denizot, F., et al. "Rapid Colorimetric Assay for Cell Growth and Survival. Modifications to the Tetrazolium Dye Procedure Giving Improved Sensitivity and Reliability." J. Immunol. Methods (1986) 89: 271-7.

(Continued)

Primary Examiner — Stacy B. Chen
(74) Attorney, Agent, or Firm — Grant Anderson LLP

(57) ABSTRACT

Methods and compositions for the optimization and production of refrigerator-temperature stable virus, e.g., influenza, compositions are provided. Formulations and immunogenic compositions comprising refrigerator-temperature stable virus compositions are provided.

22 Claims, 6 Drawing Sheets

OTHER PUBLICATIONS

Edwards, K. M., et all "A Randomized Controlled Trial of Cold-Adapted and Inactivated Vaccines for the Prevention of Influenza A Disease." J. Infect. Dis. (1994) 169: 68-76.

Flint, S. J.; et al. "Virus Cultivation, Detection, and Genetics." Principles of Virology: Molecular Biology Pathogenesis, and Control of Animal Viruses., 2000. 27-62.ASM Press Washington D.C.

Furminger, L "Vaccine Production." Textbook of Influenza., 1998. 324-332. Blackwell Oxford, UK.

Gerlier, et al. "Use of MTT Colorimetric Assay to Measure Cell Activation." J.Immunol.Methods (1986) 94: 57-63.

Heeg, K., et al. "A Rapid Colorimetric Assay for the Determination ofIL-2- Producing Helper T Cell Frequencies." I.Immuno1.Methods (1985) 77: 237-46.

Ikizler, M. R., et al. "Thermostabilization of Egg Grown Influenza Viruses." Vaccine (2002) 20: 1393-9.

International Search Report and Written Opinion mailed on: Dec. 29, 2005 in International application No. PCT/US05/35614 filed on Oct. 4, 2005.

Maassab et al.. "Evaluation of a Cold-Recombinant Influenza Virus Vaccine in Ferrets", J. of Infectious Diseases. 146:780-900; (1982).

Maassab, Adaptation and growth characteristics of influenza virus at 25 degrees C Nature. 213:612-614 (1967).

Maassab, H. F., et al. "The Development of Live Attenuated Cold-Adapted Influenza Virus Vaccine for Humans." Reviews in medical virology 9.4 (1999): 237-44.

Merten, O. W., et al "*Production a/Influenza Virus in Ce1! Cultures/or Vaccine Preparation*." Adv.Exp.Med.Biol (1996) 397: 141-51.

Mosmann, T "Rapid Colorimetric Assay for Cellular Growth and Survival: Application to Proliferation and Cytotoxicity Assays." J. Immunol. Methods (1983) 65: 55-63.

Murphy, B. R., et al "Principles Underlying the Development and use of Live Attenuated Cold-Adapted Influenza A and B Virus Vaccines." Viral Immunol. (2002) 15: 295-323.

Nichol, K. L., et al. "Effectiveness of Live, Attenuated Intranasal Influenza Virus Vaccine in Healthy, Working Adults: A Randomized Controlled Trial" *JAMA* (1999) 282: 137-44.

Reimer, C. B., et all "Influenza Virus Purification with the Zonal Ultracentrifuge." Science (1966) 152:1379-89.

Tada, H., et al. "An Improved Colorimetric Assay for Interleukin 2." J.Immunol.Methods (1986) 93: 157-165.

Vistica, D. T, et a1. "Tetrazolium-Based Assays for Cellular Viability: A Critical Examination of Selected Parameters Affecting Formazan Production." Cancer Res. (1991) 51: 2515-20.

Wareing, et al., "Immunological and Isotype-Specific responses to Russian and US Cold-Adapted Influenza a Vaccine Donor A/Leningrad/134/17/57, A/Leningrad/134/47/57, and A/Ann Arbor/6/60 (H2N2) in Mice," J.Med.Virol. (2001) 65:171-177.

Wareing, M. D., et al. "Preparation and Characterization of Attenuated Cold-Adapted Influenza A Reassortants Derived from the AlLeningradl1341I7/57 Donor Strain." Vaccine (2002) 20: 2082-90.

Yannarell, D. A., et al. "Stabilizing Cold-Adapted Influenza Virus Vaccine Under various Storage Conditions." J.Virol.Methods (2002)102: 15-25.

*ADIS R&D Profile*, "Influenza Virus Vaccine Live Intranasal-Medlmmune Vaccines," *Drugs in R&D*. vol. 4, No. 5, 2003, pp. 312-319.

Supplementary European Search Report mailed Aug. 8, 2007 in European Application No. 04775805.7 filed on Feb. 25, 2004.

Partial Supplementary European Search Report mailed on: May 18, 2007 in European Application No. 04775805.7 filed on Feb. 25, 2004.

Extended European Search Report mailed May 11, 2010 in European Application No. 05804424.6 filed on Oct. 4, 2005.

International Search Report and Written Opinion mailed on: Jan. 7, 2005 in International application No. PCT/US04/05697 filed on Feb. 25, 2004.

Luytjes et al., "Amplification, expression, and packaging of foreign gene by influenza virus," 1989, Cell, 59:1107-1113.

Zakha et al., In purification of Fermentation Products, pp. 51-69, ACS Symposium Series American Chemical Society, Washington, DC. 1985.

Belshe et al., "Influenza Vaccine-Live," Vaccines, $4^{th}$ edition, 2003, Chapter 18, pp. 371-388.

Maassab et al., "Development and characterization of cold-adapted viruses for use as live virus vaccines," Vaccine, vol. 3; pp. 355-369, 1985.

Miyazaki, C., "Experience gained using live-vaccine and future expectation," Influenza, Jul. 1, 2004, vol. 5. No. 3, 243-247 (Original Japanese document with certified English language translation).

Children's Influenza Vaccine Study Information Leaflet and Informed Consent Form, CAIV-T Liquid Formulation A prospective, randomized, double-blind, Placebo-Controlled Trial to Compare the Safety, Tolerability, Immunogenicity and Efficacy of One Dose, and Two Doses of a Influenza Virus Vaccine, Trivalent, Types A & B, Live Cold-Adaptive (CAIV-T) Compared with Placebo in Healthy Children. (Protocol No. D153-P504 Version 1 (SAMA Ethics Committee Version) South Africa, Dec. 4, 2000).

Influenza (*Flu) Vaccine Study in Children Aged 6 Month to 72 Months, CAIV-T, Liquid Formulation, Influenza Vaccine Study (Safety and Efficacy of an Influenza Vaccine, Trivalent, Types A & B in Children with Recurrent RTIS) Wyeth Lederle Vaccine Study Master English D153P514 Version 16, Apr. 2002.

Patient Information and Consent Form titled: "A prospective, randomized, double-blind, Placebo-Controlled Trial to Compare the Safety, Tolerability, Immunogenicity and Efficacy of One Dose, and Two Doses of a Influenza Virus Vaccine, Trivalent, Types A & B, Live Cold-Adaptive (CAIV-T) Administered Concomitantly with Live Attenuated, Poliovirus in Healthy Children," Protocol No. P153-P511, Jan. 2002-May 2002.

Sample Informed Consent Forms, for: "A Viron Study AL002: A Prospective Randomized, Open-Label Trial to Assess the Safety, Tolerability, Infectivity and Immunogenicity of Liquid Influenza Virus, Trivalent, Types A& B, Live, Cold-Adapted (Liquid FluMist™) Compared to Frozen FluMist™ in Children and Adults," Oct. 16, 1998.

Extended European Search Report dated: Jun. 28, 2012 in European Application No. EP12155639 filed: Feb. 25, 2004.

Kalbfuss et al., "Harvesting and concentration of human influenza A virus produced in serum-free Mammalian cell culture for the production of vaccines." Biotechnology and Bioengineering, Wiley & Sons, Hoboken, NJ, US, vol. 97, No. 1, Jun. 18, 2006, pp. 73-85.

Kistner et al., "Development of a mammalian cell (Vero) derived candidate influenza virus vaccine," Vaccine, vol. 16, No. 9-10, May 6, 1998, pp. 960-968.

Zahka et al., Practical Aspects of Tangential Flow Filtration in Cell Separations, Purification of Fermentation Products, Jan. 8, 1985, American Chemical Society, Washington DC vol. 271, pp. 51-69.

* cited by examiner

CTM-1 Process Flow

DEVELOPMENT HISTORY REPORT- LIQUID FLUMIST

CTM-1 Process Flow

Centrifuge Loading and Temperature Studies

| Strain | Lot Number | Clar. VH Volume (mL) | Clar. VH Titer (Log$_{10}$ TCID$_{50}$/mL) | Total Particles for Load (Clar. VH) | DCP Vol (mL) | DCP Titer (Log$_{10}$ TCID$_{50}$/mL) | Mono. Bulk (MB) (mL) | MB Titer (Log$_{10}$ TCID$_{50}$/mL) | Total Particles for DCP or MB | Step Yield |
|---|---|---|---|---|---|---|---|---|---|---|
| 5K eggs batch at 14°C centrifuge temp. | | | | | | | | | | |
| B/Harbin | CAZ017 | 34700 | 7.3 | 6.92E+11 | 2200 | 8.0 | N/A* | N/A* | 2.2E+11 | 32 |
| 10K eggs batch at 14°C centrifuge temp. | | | | | | | | | | |
| B/Harbin | CAZ 015 | 74500 | 7.1 | 9.38E+11 | 3000 | 8.2 | N/A* | N/A* | 4.75E+11 | 51 |
| A/Sydney | CAZ 018 | 70000 | 7.6 | 2.66E+12 | 2106 | 8.7 | N/A* | N/A* | 1.06E+12 | 40 |
| A/Beijing | CAZ 020 | 79000 | 8.6 | 3.15E+13 | 2900 | 10.3 | N/A* | N/A* | 5.79E+13 | 184 |
| A/Sydney | CAZ 022 | 54000 | 8.4 | 1.36E+13 | 3004 | 9.9 | N/A* | N/A* | 2.39E+13 | 176 |
|  | Average |  |  |  |  |  |  |  |  | 113 |
| 20K eggs batch at 14°C centrifuge temp. | | | | | | | | | | |
| B/Harbin | CAZ 016 | 95500 | 7.7 | 4.79E+12 | 3300 | 8.9 | N/A* | N/A* | 2.62E+12 | 55 |
| A/Sydney | CAZ 019 | 119000 | 7.6 | 4.22E+12 | N/A | N/A | 4200 | 8.6 | 1.67E+12 | 40 |
| A/Beijing | CAZ 021 | 129000 | 8.8 | 8.14E+13 | 3600 | 10 | N/A* | N/A* | 3.60E+13 | 44 |
|  | Average |  |  |  |  |  |  |  |  | 46 |

N/A = Not Available

N/A* = Not Applicable

[1]Data extracted from "Fact on Loading Studies", except for CAZ 015 and 022

[2]Data extracted from "Fact on Loading Studies", except for CAZ 018, 019, 021 and 022

FIG. 3

Liquid FLUMIST

TABLE 2.3.1.1 A
CTM-1
Summary of QC Test Data – In Process Assay Results

| | B/Harbin/07/94-like | | | A/Sydney/05/97 | | | | A/Beijing/262/95 | | |
|---|---|---|---|---|---|---|---|---|---|---|
| | CAZ026 | CAZ027 | CAZ028 | CAZ025 | CAZ029 | CAZ030 | CAZ034 | CAZ031 | CAZ032 | CAZ033 |
| In-Process Assays | | | | | | | | | | |
| Potency by TCID$_{50}$ (log$_{10}$mL$^{-1}$)*** | | | | | | | | | | |
| • Virus Harvest (Unstabilized) | 8.1 | 8.25 | 8.65 | 8.8 | 7.5 | 6.0 | 7.6 | 9.25 | 8.3 | 8.85 |
| • Stabilized Virus Harvest | 7.8 | 8.2 | 8.3 | 7.85 | 7.7 | 7.1 | 7.55 | 9.2 | 9.35 | 9.2 |
| • Clarified Virus Harvest | 7.7 | 7.8 | 8.75 | 8.1 | 7.4 | 6.8 | 7.35 | 8.9 | 8.65 | 9.8 |
| • Flow Through (Zonal Supernate) | 7.15 | 8.3 | 7.65 | 7.2 | 6.7 | 6.1 | 7.15 | 8.6 | 8.35 | 8.55 |
| • Centrifuge Peak Fraction Pool | 9.0 | 9.25 | 8.7 | 8.8 | 9.45 | 8.7 | 9.2 | 10.4 | >10.2 | 10.5 |
| • Diluted Centrifuge Peak Fraction Pool | 8.55 | 8.5 | 9.65 | 8.55 | 8.7 | 8.9 | 8.75 | 10.2 | 10.1 | 9.75 |
| • Monovalent Bulk (Sterile Filtered Zonal Concentrate) | 8.35 | 8.4 | 9.85 | 8.55 | 8.35 | *5.9 | 7.9 | 10.0 | 9.75 | 9.3 |
| BioBurden (cfu/ml) | | | | | | | | | | |
| • Virus Harvest (Unstabilized) | 80 | >100 | <1 | <1 | >100 | >100 | >100 | >100 | <1 | >100 |
| • Stabilized Virus Harvest | 15 | >100 | <1 | <1 | >100 | >100 | >100 | >100 | >100 | >100 |
| • Diluted Centrifuge Peak Fraction Pool | 23 | >100 | <1 | <1 | <1 | <1 | >100 | <1 | >100 | >100 |
| Endotoxin (Eu/mL) | | | | | | | | | | |
| • Monovalent Bulk (Sterile Filtered Zonal Concentrate) | 135.8 | 586.9 | **258.9 | 52.84 | 36.27 | 263.2 | <5 | 11.43 | 21.67 | 25.39 |
| Sucrose Concentration (%) | | | | | | | | | | |
| • Centrifuge Peak Fraction Pool | 42.05 | 40.65 | 39.85 | 40.6 | 39.1 | 31.6 | 40.4 | 40.65 | 43.45 | 41.2 |
| • Monovalent Bulk (Sterile Filtered Zonal Concentrate) | 7.5 | 7.5 | 7.6 | 7.5 | 7.5 | 7.4 | 7.7 | 7.9 | 7.5 | 8.1 |

*CAZ030 was not accepted for further processing due to low titer  Endotoxin sample from Harvest Stage  *Average of QC reported Values

FIG. 4

Liquid
FLUMIST

TABLE 2.3.1.1 B
CTM-1
Average Yields for A/Beijing, A/Sydney, B/Harbin

| Process Step | Strain | | | | | |
|---|---|---|---|---|---|---|
| | A/Beijing[1] | | A/Sydney[2] | | B/Harbin[3] | |
| | % Step Yield | % Overall Yield | % Step Yield | % Overall Yield | % Step Yield | % Overall Yield |
| Stabilised Virus Harvest | N/A | 100 | N/A | 100 | N/A | 100 |
| Clarified Virus Harvest | 147 | 147 | 78 | 78 | 125 | 125 |
| Centrifuge Peak Fraction Pool | 19 | 10 | 60 | 30 | 14 | 8 |
| Diluted Centrifuge Peak Fraction Pool | 391 | 35 | 441 | 124 | 2158 | 75 |
| Monvalent Bulk | 42 | 16 | 30 | 13 | 89 | 93 |

[1] Average of step and overall yields from table 2.3.1.2C
[2] Average of step and overall yields from table 2.3.1.3C
[3] Average of step and overall yields from table 2.3.1.4C Note: the % overall yield values above were calculated as the average of the % overall yield values for each process step from tables 2.3.1.2C, 2.3.1.3C, and 2.3.1.4C. As a result, the % overall yields at each step are not consistent with the % overall yields that would be calculated by multiplying each successive % step yields in this table. The calculation method used here better reflects the actual process yields through the campaign.

FIG. 5

TABLE 2.3.1.1 C

Liquid FLUMIST

CTM-1 Summary of QC Test Data – Monovalent Bulk Release Assay Results

| | | B/Harbin/07/94-like | | | A/Sydney/05/97 | | | | A/Beijing/262/95 | | |
|---|---|---|---|---|---|---|---|---|---|---|---|
| | | CAZ026 | CAZ027 | CAZ028 | CAZ025 | CAZ029 | CAZ030 | CAZ034 | CAZ031 | CAZ032 | CAZ033 |
| Certificate of Analysis (C of A) Assays<br>ASSAY | SPECIFICATION | | | | | | | | | | |
| Virus Harvest (Unstabilized) | | | | | | | | | | | |
| • Mycoplasma | None detected | Pass | Pass | Pass | Pass | Pass | NA | Pass | Pass | Pass | Pass |
| • M. tuberculosis | None detected | Pass | Pass | Pass | Pass | Pass | NA | Pass | Pass | Pass | Pass |
| • ALV (ELISA) | No ALV detected | Pass | Pass | Pass | Pass | Pass | NA | Pass | Pass | Pass | Pass |
| • Extraneous virus<br>In vitro<br>In vivo | No extraneous virus detected | Pass | Pass | Pass | Pass | Pass | NA | Pass | Pass | Pass | Pass |
| • RT Assay | Neg. for RT enzyme | Pass | Pass | Pass | Pass | Pass | NA | Pass | Pass | Pass | Pass |
| • Genotype | 2 WT genes/6 CA genes | Pass | Pass | Pass | Pass | Pass | NA | Pass | Pass | Pass | Pass |
| • Phenotype | ca and ts genes | Pass | Pass | Pass | Pass | Pass | NA | Pass | Pass | Pass | Pass |
| • Attenuation | No flu-like symptoms in ferrets | Pass | Pass | Pass | Pass | Pass | NA | Pass | Pass | Pass | Pass |
| • Identity $TCID_{50}$<br>Neutralized<br>Un-neutralized | <br>No cytopathic effect<br>Cytopathic effect | <br><1.3<br>8.7 | <br><1.3<br>8.3 | <br><1.4<br>8.6 | <br><1.3<br>9.1 | <br><1.3<br>7.9 | <br>NA<br>NA | <br><1.3<br>8.2 | <br><1.3<br>9.65 | <br><1.3<br>8.8 | <br><1.3<br>9.1 |
| Monovalent Bulk (sterile filtered zonal concentrate) | | | | | | | | | | | |
| • Sterility | | Pass | Pass | Pass | Pass | Pass | NA | Pass | Pass | Pass | Pass |
| Lot Disposition | | Release | Release | Release | Release | Release | Rejected | Release | Release | Release | Release |

NA – Not Applicable (assay not performed)

FIG. 6

REFRIGERATOR-TEMPERATURE STABLE INFLUENZA VACCINE COMPOSITIONS

CROSS REFERENCE TO RELATED APPLICATIONS

This application is a continuation of U.S. patent application Ser. No. 11/242,018, filed Oct. 4, 2005, now abandoned, which claims the benefit under 35 U.S.C. §119(e) of U.S. Provisional Application No. 60/616,711, filed on Oct. 6, 2004; and is a continuation-in-part of and claims the benefit under 35 U.S.C. §120 of U.S. patent application Ser. No. 10/788,236, filed Feb. 25, 2004, now U.S. Pat. No. 7,262,045, which claims the benefit under 35 U.S.C §119(e) of U.S. Provisional Application No. 60/450,181, filed Feb. 25, 2003. All of the foregoing applications are incorporated herein by reference in their entirety.

BACKGROUND OF THE INVENTION

Vaccines against various and evolving strains of influenza are important not only from a community health stand point, but also commercially, since each year numerous individuals are infected with different strains and types of influenza virus. Infants, the elderly, those without adequate health care and immunocompromised persons are at special risk of death from such infections. Compounding the problem of influenza infections is that novel influenza strains evolve readily, thereby necessitating the continuous production of new vaccines.

Numerous vaccines capable of producing a protective immune response specific for such different influenza viruses have been produced for over 50 years and include, e.g., whole virus vaccines, split virus vaccines, surface antigen vaccines and live attenuated virus vaccines. However, while appropriate formulations of any of these vaccine types are capable of producing a systemic immune response, live attenuated virus vaccines have the advantage of being also able to stimulate local mucosal immunity in the respiratory tract. A vaccine comprising a live attenuated virus that is capable of being quickly and economically produced and that is capable of easy storage/transport is thus quite desirable. Even more desirable would be such a vaccine that would be capable of storage/transport at refrigerator temperatures (e.g., approximately 2-8° C.).

To date, all influenza vaccines commercially available in the U.S. have been propagated in embryonated hen eggs. Although influenza virus grows well in hen eggs, the production of vaccine is dependent on the availability of such eggs. Because the supply of eggs must be organized, and strains for vaccine production selected months in advance of the next flu season, the flexibility of this approach can be limited, and often results in delays and shortages in production and distribution. Therefore, methods to increase stability (e.g., at refrigerator temperatures) of the produced vaccine, are greatly desirable as they can prevent deterioration of vaccine stock, which would otherwise necessitate new production, etc.

Systems for producing influenza viruses in cell culture have also been developed in recent years (See, e.g., Furminger. *Vaccine Production*, in Nicholson et al. (eds.) Textbook of Influenza pp. 324-332; Merten et al. (1996) *Production of influenza virus in cell cultures for vaccine preparation*, in Cohen & Shafferman (eds.) Novel Strategies in Design and Production of Vaccines pp. 141-151); therefore, any methods to increase vaccine composition stability (e.g., storage/transport at refrigerator temperature) in these systems as well are also greatly desirable.

Considerable work in the production of influenza virus for production of vaccines has been done by the present inventors and co-workers; see, e.g., U.S. patent application Nos. 60/375,675 filed Apr. 26, 2002, PCT/US03/12728 filed Apr. 25, 2003, Ser. No. 10/423,828 filed Apr. 25, 2003, and PCT/US05/017734 filed May 20, 2005.

The present invention provides vaccine compositions that have stability at, for example, refrigerator temperatures (e.g., 4° C.) and methods of producing the same. Aspects of the current invention are applicable to traditional hen egg and new cell culture vaccine production methods (and also combined systems) and comprise numerous other benefits that will become apparent upon review of the following.

SUMMARY OF THE INVENTION

The current invention provides liquid vaccine formulations that are substantially stable at temperatures ranging from 4° C. to 8° C. These and other liquid formulations, which are specific embodiments of the invention are referred to herein, for example, as "vaccine formulations of the invention," "refrigerator stable vaccine formulations," "liquid formulations of the invention," "formulations of the invention," "refrigerator-temperature stable (RTS) formulations of the invention," or simply "compositions of the invention" or "virus compositions of the invention."

The present invention provides liquid vaccine formulations that are substantially stable at temperatures ranging from 4° C. to 8° C. In one specific embodiment of the invention, liquid vaccine formulations of the invention are substantially stable at temperatures ranging from 2° C. to 8° C. or at 4° C. for a period of 3 months, or 4 months, or 5 months, or 6 months, or 9 months, or 12 months, or 18 months, or 24 months, or 36 months, or 48 months, in that there is an acceptable loss of potency (e.g., influenza virus potency loss), for example, a potency loss of between 0.5-1.0 logs, or less than 0.5 logs, or less than 1.0 logs of potency, at the end of such time.

In one embodiment, refrigerator stable vaccine formulations of the invention are provided that comprise live influenza viruses. For instance, formulations of the invention may comprise one or more of the following: an attenuated influenza virus, a cold-adapted influenza virus, a temperature-sensitive influenza virus, an attenuated cold-adapted temperature sensitive influenza virus, an influenza A virus, and an influenza B virus. In one embodiment, liquid vaccine formulations of the invention comprise two influenza A virus strains and one influenza B virus strains.

Alternatively, formulations of the invention may comprise other live viruses such as paramyxoviruses (e.g., RSV, measles virus, mumps virus, Sendai, New Castle Disease viruses) and parainfluenza virus.

The present invention further provides immunogenic compositions comprising formulations of the invention. The present invention further provides vaccines (e.g., influenza vaccines) comprising formulations and immunogenic compositions of the invention.

The present invention further includes methods of producing such liquid vaccine formulations. For instance, in one specific embodiment, methods of producing liquid formulations comprising one or more influenza viruses are provided herein. In one specific embodiment, methods of producing a liquid formulation of the invention includes one or more of the following steps: 1) introducing a plurality of vectors [one or more of which incorporates (or encodes) a portion of an influenza virus genome] into a population of host eggs or into a population of host cells, which population of host eggs or host cells is capable of supporting replication of influenza virus; 2) culturing the population of host eggs or population of host cells at an appropriate temperature; 3) recovering influenza viruses in a viral harvest; 4) addition of a stabilizer (e.g., sucrose and glutamate-containing solutions as described herein); 5) clarifying the viral harvest (e.g., by depth or membrane filtration), thereby producing a clarified viral harvest; 6) subjecting the viral harvest to a centrifugation step (e.g., continuous zonal centrifugation, continuous flow centrifugation); 7) a sterile filtration step (e.g., use of 0.2, or 0.2-0.5 micron filter (with or without heating during filtration); and 8) storage at −60 degrees C.

In another specific embodiment, methods of producing a liquid formulation of the invention includes one or more of the following steps: 1) infection of a population of host eggs or into a population of host cells with influenza viruses; 2) culturing the population of host eggs or population of host cells at an appropriate temperature; 3) recovering influenza viruses in a viral harvest; 4) addition of a stabilizer; 5) clarifying the viral harvest (e.g., by depth filtration and/or passing through one or more filters ranging from 0.2-0.8 microns; or 0.8 or 1.5 micron followed by 0.2 micron), thereby producing a clarified viral harvest; 6) subjecting the viral harvest to a centrifugation step (e.g., continuous zonal centrifugation, continuous flow centrifugation); 7) a sterile filtration step (e.g., use of 0.2, or 0.2-0.5 micron filter (with or without heating during filtration); and 8) storage at −60 degrees C.

In other specific embodiment, methods of producing an influenza virus composition of the invention comprises one or more of the following steps: 1) infection of a population of host eggs or into a population of host cells with influenza viruses; 2) culturing the population of host eggs or population of host cells at an appropriate temperature; 3) recovering influenza viruses in a viral harvest; 4) clarifying the viral harvest by filtration, thereby producing a clarified viral harvest; 5) subjecting the clarified viral harvest to centrifugation (e.g., continuous flow centrifugation), thereby producing a further clarified viral harvest; 6) addition of stabilizers (e.g., one or more of the following: 6-8% sucrose; 1-2% arginine monohydrochloride; 0.05-0.1% glutamic acid, monosodium monohydrate; and 0.5-2% gelatin hydrolysate); and 6) sterilizing said further clarified viral harvest by filtration.

In other specific embodiment, methods of producing an influenza virus composition of the invention comprises all of the following steps: 1) infection of a population of host eggs or into a population of host cells with influenza viruses; 2) culturing the population of host eggs or population of host cells at an appropriate temperature; 3) recovering influenza viruses in a viral harvest; 4) clarifying the viral harvest by filtration, thereby producing a clarified viral harvest; 5) subjecting the clarified viral harvest to centrifugation (e.g., continuous flow centrifugation), thereby producing a further clarified viral harvest; and 6) sterilizing said further clarified viral harvest by filtration.

In other specific embodiment, methods of producing an influenza virus composition of the invention comprises one or more of the following steps: 1) infection of a population of host eggs or into a population of host cells with influenza viruses; 2) culturing the population of host eggs or population of host cells at an appropriate temperature; 3) recovering influenza viruses in a viral harvest; 4) clarifying the viral harvest; 5) subjecting the clarified viral harvest to centrifugation (e.g., continuous flow centrifugation), thereby producing a further clarified viral harvest; and 6) sterilizing said further clarified viral harvest by filtration.

In other specific embodiment, methods of producing an influenza virus composition of the invention comprises one or more of the following steps: 1) infection of a population of host eggs or into a population of host cells with influenza viruses; 2) culturing the population of host eggs or population of host cells at an appropriate temperature; 3) recovering influenza viruses in a viral harvest; 4) clarifying the viral harvest; and 5) subjecting the clarified viral harvest to diafiltration.

In other specific embodiment, methods of producing an influenza virus composition of the invention comprise one or more of the following steps: 1) infection of a population of host eggs or into a population of host cells with influenza viruses; 2) culturing the population of host eggs or population of host cells at an appropriate temperature; 3) recovering influenza viruses in a viral harvest; 4) clarifying the viral harvest; 5) subjecting the clarified viral harvest to diafiltration; and 6) addition of stabilizers (e.g., one or more of the following: 6-8% sucrose; 1-2% arginine monohydrochloride; 0.05-0.1% glutamic acid, monosodium monohydrate; and 0.5-2% gelatin hydrolysate).

These and other objects and features of the invention will become more fully apparent when the following detailed description is read in conjunction with the accompanying figures appendix.

BRIEF DESCRIPTION OF THE DRAWINGS

FIG. 3: Displays a table illustrating Centrifuge Loading and Temperature Studies.

FIG. 4: Displays a table illustrating a Summary of QC test data.

FIG. 5: Displays a table illustrating average yields for a number of influenza strains.

FIG. 6: Displays a table with a summary of QC test data for monovalent bulk release assay results.

DETAILED DESCRIPTION

Figure 1:
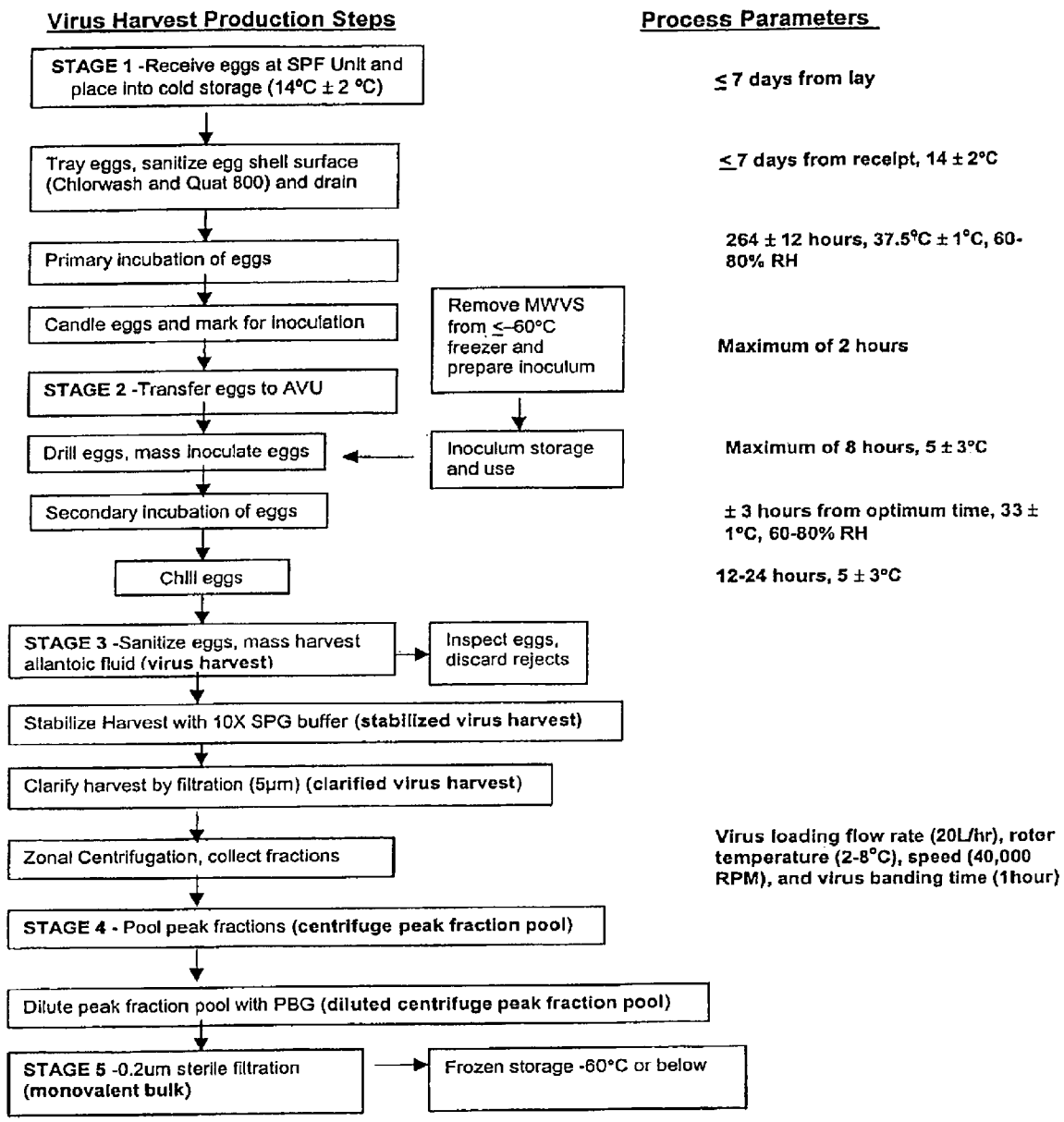
FIG. 1: Displays a flow chart illustrating a CTM Process Flow.

The present invention provides liquid vaccine formulations that are substantially stable at temperatures ranging from 4° C. and 8° C. In one specific embodiment of the invention, liquid vaccine formulations of the invention are substantially stable at temperature ranging from 2-8° C. or 4° C. for a period of at least 1 month, or at least 2 months, or at least 3 months, or at least 4 months, or at least 5 months, or at least 6 months, or at least 9 months, or at least 12 months, or at least 18 months, or at least 24 months, or at least 36 months, or at least 48 months, in that there is an acceptable loss of potency (e.g., influenza virus potency loss) at the end of such time, for example, a potency loss of between 0.5-1.0 logs (as measured by, e.g., $TCID_{50}$ or Fluorescent Focus Assay (FFA).

The present invention provides liquid vaccine formulations that are substantially stable at temperatures ranging from 4° C. and 8° C. In one specific embodiment of the invention, liquid vaccine formulations of the invention are substantially stable at temperature ranging from 2-8° C. or 4° C. for a period of at least 1 month, or at least 2 months, or at least 3 months, or at least 4 months, or at least 5 months, or at least 6 months, or at least 9 months, or at least 12 months, or at least 18 months, or at least 24 months, or at least 36 months, or at least 48 months, in that there is an acceptable loss of potency (e.g., influenza virus potency loss) at the end of such time, for example, a potency loss of less than 10%, or less than 20%, or less than 30%, or less than 40%, or less than 50%, or less than 60%, or less than 70%, or less than 80%, or less than 90%.

The present invention further provides immunogenic compositions comprising formulations of the invention. The present invention further provides vaccines (e.g., influenza vaccines) comprising formulations and/or immunogenic compositions of the invention.

In one embodiment, liquid vaccine formulations of the invention are provided that comprise live influenza viruses. For instance, formulations of the invention may comprise one or more of the following: an attenuated influenza virus, a cold-adapted influenza virus, a temperature-sensitive influenza virus, an attenuated cold-adapted temperature sensitive influenza virus, an influenza A virus, and an influenza B virus. In one embodiment, liquid vaccine formulations of the invention comprise two influenza A virus strains and one influenza B virus strains.

Alternatively, formulations of the invention may comprise other live viruses such as paramyxoviruses (e.g., RSV, parainfluenza virus, measles virus, mumps virus, Sendai, New Castle Disease viruses).

The present invention further includes methods of producing such liquid vaccine formulations. For instance, in one specific embodiment, methods of producing liquid formulations comprising one or more influenza viruses are provided herein. In one specific embodiment, methods of producing a liquid formulation of the invention includes one or more of the following steps: 1) introducing a plurality of vectors [one or more of which incorporates (or encodes) a portion of an influenza virus genome] into a population of host eggs or into a population of host cells, which population of host eggs or host cells is capable of supporting replication of influenza virus; 2) culturing the population of host eggs or population of host cells at an appropriate temperature; 3) recovering influenza viruses in a viral harvest; 4) addition of a stabilizer (e.g., sucrose and glutamate-containing solutions as described herein); 5) clarifying the viral harvest (e.g., by depth or membrane filtration), thereby producing a clarified viral harvest; 6) subjecting the viral harvest to a centrifugation step (e.g., continuous zonal centrifugation, continuous flow centrifugation); 7) a sterile filtration step (e.g., use of 0.2, or 0.2-0.5 micron filter (with or without heating during filtration); and 8) storage at −60 degrees C.

In another specific embodiment, methods of producing a liquid formulation of the invention includes one or more of the following steps: 1) infection of a population of host eggs or into a population of host cells with influenza viruses; 2) culturing the population of host eggs or population of host cells at an appropriate temperature; 3) recovering influenza viruses in a viral harvest; 4) addition of a stabilizer; 5) clarifying the viral harvest (e.g., by depth filtration and/or passing through one or more filters ranging from 0.2-0.8 microns; or 0.8 or 1.5 micron followed by 0.2 micron), thereby producing a clarified viral harvest; 6) subjecting the viral harvest to a centrifugation step (e.g., continuous zonal centrifugation, continuous flow centrifugation); 7) a sterile filtration step (e.g., use of 0.2, or 0.2-0.5 micron filter (with or without heating during filtration); and 8) storage at −60 degrees C.

In other specific embodiment, methods of producing an influenza virus composition of the invention comprises one or more of the following steps: 1) infection of a population of host eggs or into a population of host cells with influenza viruses; 2) culturing the population of host eggs or population of host cells at an appropriate temperature; 3) recovering influenza viruses in a viral harvest; 4) clarifying the viral harvest by filtration, thereby producing a clarified viral harvest; 5) subjecting the clarified viral harvest to centrifugation (e.g., continuous flow centrifugation), thereby producing a further clarified viral harvest; 6) addition of stabilizers (e.g., one or more of the following: 6-8% sucrose; 1-2% arginine monohydrochloride; 0.05-0.1% glutamic acid, monosodium monohydrate; and 0.5-2% gelatin hydrolysate); and 6) sterilizing said further clarified viral harvest by filtration.

In other specific embodiment, methods of producing an influenza virus composition of the invention comprises all of the following steps: 1) infection of a population of host eggs or into a population of host cells with influenza viruses; 2) culturing the population of host eggs or population of host cells at an appropriate temperature; 3) recovering influenza viruses in a viral harvest; 4) clarifying the viral harvest by filtration, thereby producing a clarified viral harvest; 5) subjecting the clarified viral harvest to centrifugation (e.g., continuous flow centrifugation), thereby producing a further clarified viral harvest; and 6) sterilizing said further clarified viral harvest by filtration.

In other specific embodiment, methods of producing an influenza virus composition of the invention comprises one or more of the following steps: 1) infection of a population of host eggs or into a population of host cells with influenza viruses; 2) culturing the population of host eggs or population of host cells at an appropriate temperature; 3) recovering influenza viruses in a viral harvest; 4) clarifying the viral harvest; 5) subjecting the clarified viral harvest to centrifugation (e.g., continuous flow centrifugation), thereby producing a further clarified viral harvest; and 6) sterilizing said further clarified viral harvest by filtration.

In other specific embodiment, methods of producing an influenza virus composition of the invention comprises one or more of the following steps: 1) infection of a population of host eggs or into a population of host cells with influenza viruses; 2) culturing the population of host eggs or population of host cells at an appropriate temperature; 3) recovering influenza viruses in a viral harvest; 4) clarifying the viral harvest; and 5) subjecting the clarified viral harvest to diafiltration.

In other specific embodiment, methods of producing an influenza virus composition of the invention comprise one or more of the following steps: 1) infection of a population of host eggs or into a population of host cells with influenza viruses; 2) culturing the population of host eggs or population of host cells at an appropriate temperature; 3) recovering influenza viruses in a viral harvest; 4) clarifying the viral harvest; 5) subjecting the clarified viral harvest to diafiltration; and 6) addition of stabilizers (e.g., one or more of the following: 6-8% sucrose; 1-2% arginine monohydrochloride; 0.05-0.1% glutamic acid, monosodium monohydrate; and 0.5-2% gelatin hydrolysate).

In one embodiment, methods of producing a liquid formulation of the invention may include the step of freezing such formulations. The freezing step may be done, for example, prior to final stability testing and distribution and/or prior to storage at refrigerator temperatures (e.g., 4-8 degrees Celsius). Freezing the vaccine formulations prior to storage under refrigerator temperatures may increase stability of the vaccine formulations of the invention by at least 10%, or at least 20%, or at least 30%, or at least 40%, or at least 50%, or at least 80%.

The invention further provides methods of producing one or more influenza virus compositions by filtering an influenza virus harvest, whereby the virus harvest is heated during the filtering. Included in these specific embodiments, the filtering comprises passage of the composition through a microfilter of a pore size ranging from 0.2 micrometers to about 0.45 micrometers. Furthermore, in various embodiments, the temperature of heating in such embodiments optionally comprises from about 28° C. to about 40° C. or more, while in some embodiments, the temperature comprises 31° C. or from about 30° C. to about 32° C. The heating in such embodiments optionally occurs before or during or before and during the filtration and optionally comprises from about 50 minutes to about 100 minutes, from about 60 minutes to about 90 minutes, or about 60 minutes. The invention also provides an influenza virus composition produced by such methods (including wherein the composition is a vaccine composition).

Stabilizers and Buffers

Stabilizers of the invention include, for example, one or more of the following: arginine (e.g., 0.5-1%, 1-2%; 1%; 1.2%; 1.5%, 0.75-2%); poloxamer; sucrose (e.g., 2-8%; 2%; 6-8%; 3%; 4%; 5%; 6%; 7%, or 8%); hydrolyzed gelatin (e.g., 1%; 0.5-2%; 1.5%; 0.5%; 0.75%); and glutamate (e.g., 0.05-0.1%, 0.02-0.15%, 0.03%, 0.04%, 0.06%, 0.02-0.3%, or 0.094%)

Buffers of the invention include, for example, one or more of the following: phosphate buffer (mono or dibasic or both) (e.g., 10-200 mM, pH 7-7.5; 100 mM, pH 7.2; 100 mM, pH 7-7.3); and histidine buffers (e.g., 25-50 mM histidine, pH 7-7.5, 50-100 mM Histidine, pH 7-7.5).

Process Yield

In one embodiment, methods of producing a liquid formulation of the invention results in an actual or average process yield (from Viral Harvest (VH) to final formulation) of less than 10%, of less than 16%, less than 20%, less than 30%, less than 40%, less than 50%, less than 60%, less than 70%, less than 80%, less than 90%, or less than 93%, or less than 95%.

It will be appreciated by those skilled in the art that the various steps of the methods described herein are not required to be performed or required to exist in the same production series. Thus, while in some preferred embodiments, all steps and/or compositions herein are performed or exist, in other embodiments, one or more steps are optionally, e.g., omitted, changed (in scope, order, placement, etc.) or the like.

It will also be appreciated by those skilled in the art that typical embodiments comprise steps/methods/compositions that are known in the art, e.g., candling of virus containing eggs, inoculation of eggs with viruses, etc. Therefore, those skilled in the art are easily able to determine appropriate conditions, sub-steps, step details, etc., for such known steps to produce the appropriate viruses, virus solutions, compositions, etc. essentially stable at 2-8° C. The individual steps are described in greater detail below.

Further, the present invention provides methods of using such liquid vaccine formulations. For example, vaccine formulations may be administered to a human in order to prevent or reduce the effects of a viral infection, e.g., influenza infection. In one embodiment, formulations of the invention are administered as an immunogenic composition to prevent or reduce the effects of an influenza virus infection.

Refrigerator-stable CAIV Formulations

Prior work by the inventor and co-workers has resulted in the development of a trivalent, live, cold-adapted influenza vaccine (CAIV-T, FluMist®, which is referenced throughout as FluMist, but should be assumed to be FluMist®) administered by nasal spray. The current invention involves the development of a formulation of CAIV-T, which has improved stability profile at refrigerated temperatures. Methods of producing such improved formulations are provided herein and may include one or more of the following steps: a sterile filtration step to reduce contamination risk, ultracentrifugation (e.g., rate zonal centrifugation), and diafiltration. In addition, included herein are a number of methods of producing liquid FluMist and other refrigerator-temperature stable (RTS) formulations of the invention.

The development of CAIV strains was assisted by Dr. John Maassab of the University of Michigan in the 1960s who serially passaged influenza A and B strains in PCK cells at decreasing temperatures until the resulting strains reproducibly showed the phenotypic properties of cold-adaptation (virus grows well at reduced temperatures compared to wild type virus), temperature sensitivity (virus does not grow well in elevated temperatures in vitro), and attenuation (virus replication is restricted in ferrets). Through development by, e.g., the inventor and coworkers, these properties were used as the basis for development of an annual trivalent vaccine reflecting the CDC-designated vaccines strains for a particular year, through the process of 6:2 genetic reassortment. For example, a 6:2 CAIV strain is produced by in vitro co-infection of the relevant A or B strain Master Donor Virus (MDV) with the circulating flu strain of interest, and antibody-mediated selection of the proper reassortant. The target 6:2 reassortant contains HA and NA genes from the circulating strain, and the remaining genes from the cold adapted master donor virus (MDV). The reassortant retains the cold adapted phenotypic properties described above. Further development of CAIV has been conducted by the inventors and coworkers. FluMist has demonstrated a safe profile and shown efficacy against viral challenge and is approved for commercial pharmaceutical use in many situations.

The original formulation of FluMist contained virus harvest (VH) produced by infecting specific pathogen-free chicken eggs with Manufacturer's Working Virus Seed (MWVS) of the selected strain, followed by incubation for two to three days, and harvesting infected allantoic fluid. VH was stabilized by the addition at $\frac{1}{10}^{th}$ volume of a 10× sucrose phosphate glutamate (SPG) solution. Trivalent FluMist was produced by combining VH from each of the three strains in the vaccines for a given year with stabilized normal allantoic fluid (NAF) to a target concentration of 7.3 $\log_{10}TCID_{50}$/mL of each strain. The resulting blend was then filled into sprayers fitted with a spray tip allowing intranasal delivery of FluMist vaccine. This product format was used as "frozen FluMist", which was stored in a frozen form. It will be appreciated that the MWVS virus could also optionally be manufactured by, e.g. plasmid reassortment. See, e.g., U.S. patent application Nos. 60/375,675 filed Apr. 26, 2002, PCT/US03/12728 filed Apr. 25, 2003, Ser. No. 10/423,828 filed Apr. 25, 2003, PCT/US05/017734 filed May 20, 2005, and US20050186563.

While frozen FluMist can serve as a marked vaccine when frozen after manufacture and held frozen until time of use, a form of FluMist that is stable for transport/storage at refrigerator temperatures is quite desirable. Such "refrigerator-temperature stable" (or RTS) forms are characterized by one or more (but not necessarily all in each embodiment) of the following: retention of stability when distributed as a refrigerated liquid; are passed through sterilizing filters (e.g., 0.2 micron) to provide assurance of a sterile product; have reduced content of egg protein (e.g., substantially free of NAF); have eliminated the need for manufacture of NAF diluent; have a reduced volume of a dose; and comprises either or both arginine and gelatin as excipients (e.g., as stabilizers). In certain aspects herein, formulations having one or more such characteristics are referred to as "liquid FluMist" or RTS or various similar terms, to distinguish from other versions of CAIV-T vaccine, such as frozen. The current invention presents these and other aspects.

In producing/testing a liquid RTS virus composition of the invention, numerous development batches were conducted. Development batches ranged from 2000 to 20,000 eggs per lot, while GMP batches were approximately 10,000 eggs each. It will be appreciated that while various examples and protocols are given herein for production of MWVS viruses (e.g., reassortants), the viruses are optionally produced through different means in different embodiments. For example, in certain embodiments, the viruses herein are optionally made through the protocols shown herein, while in other embodiments, the MWVS viruses are optionally made through, e.g., plasmid reassortment or "plasmid rescue" technologies. See, e.g., U.S. patent application Nos. 60/375,675 filed Apr. 26, 2002, PCT/US03/12728 filed Apr. 25, 2003, U.S. Ser. No. 10/423,828 filed Apr. 25, 2003, Ser. No. 10/788,236 filed Feb. 25, 2004, PCT/US05/017734 filed May 20, 2005, and US20050186563, which are each incorporated by reference herein. Accordingly, as used herein "infection of a population of host cells" encompasses host cells infected by virus created by or during plasmid reassortment.

In various embodiments, the invention comprises virus and vaccine compositions that are substantially stable, e.g., do not show unacceptable losses in potency, e.g., potency loss of between 0.5-1.0 logs, or less than 0.5 logs, or less than 1.0 logs, over selected time periods (typically for at least 1 month, for at least 2 months, for at least 3 months, for at least 4 months, for at least 5 months, for at least 6 months, for at least 7 months, for at least 8 months, for at least 9 months, for at least 10 months, for at least 11 months, for at least 12 months, for at least 13 months, for at least 14 months, for at least 15 months, for at least 16 months, for at least 17 months, for at least 18 months, for at least 19 months, for at least 20 months, for at least 21 months, for at least 22 months, for at least 23 months, or for at least 24 months, or greater than 24 months, etc.) at desired temperatures (e.g., typically 4° C., 5° C., 8° C., from about 2° C. to about 8° C. or greater than 2° C., or between the ranges of 2° C. to 4° C., or between the ranges of 2° C. to 8° C.).

While a number of aspects of the invention herein are exemplified or illustrated with FluMist, the principles embodied by the invention are applicable to other virus/vaccine compositions as well and should not necessarily be limited to particular strains/viruses herein. Thus other live attenuated influenza virus and vaccines and compositions are also within the purview of the invention, e.g., ones created through rational means, by human intervention, etc. Also, other viruses of other influenza strains, etc., such as influenza A strains, influenza B strains, attenuated and non-attenuated influenza strains, cold adapted and non-cold adapted influenza strains, temperature sensitive and non-temperature sensitive influenza strains, etc. are all optionally within the embodiments of the current invention. Such other virus and vaccine can be used, e.g., as new vaccine and/or as controls for testing other vaccine either in humans or animals, etc. In addition, other live viral vaccine compositions particularly those comprising live viruses grown in chicken cells or eggs (e.g., measles virus) are embodiments of the invention. Furthermore, the principles embodied by the invention are also largely applicable to virus and vaccine compositions comprising live viruses grown in mammalian cells. See, e.g., U.S. Pat. Nos. 6,244,354; 6,146,873; and 6,656,720.

Bulk Virus Harvest Production

Purification of the cold-adapted influenza virus (or other similar viruses) and the actual formulation of the compositions are features of RTS, or liquid, virus compositions. Separation of influenza virus from allantoic fluid had been practiced as a part of commercial processes for manufacture of inactivated vaccines. The method of choice for such inactivated vaccine has been ultra-centrifugation. Commercial scale continuous flow ultracentrifuge became available in 1969 and was quickly applied to the preparation of inactivated influenza vaccines. While chromatographic purification of live influenza virus would be an attractive alternative, robust large-scale processes that retain viral activity are not yet available. This is thought to be due to the membrane coat and pleiomorphic nature of the influenza virus particle.

Recovery of live virus (as opposed to inactivated virus) purified by ultra-centrifugation was achieved by the inventors and coworkers and is an embodiment of the current invention. Further work demonstrated the ability of depth filtration as a commercially viable alternative to swinging-bucket centrifugation prior to ultra-centrifugation, and acceptable recoveries of live virus following filtration through a 0.2 micron filter, and again such is an embodiment of the current invention.

In one specific embodiment, the median process yield for the VH clarification step of the methods of the invention is at least 30%, or at least 40%, or at least 50%, or at least 60%, or at least 70%, or at least 80%, or at least 90%.

In another specific embodiment, the median process yield for the ultracentrifugation (e.g., zonal centrifugation) step of the methods of the invention is at least 30%, or at least 40%, or at least 50%, or at least 60%, or at least 70%, or at least 80%, or at least 90%.

In another specific embodiment, the median process yield for the peak dilution and sterile filtration step of the methods of the invention is at least 30%, or at least 40%, or at least 50%, or at least 60%, or at least 70%, or at least 80%, or at least 90%.

The ultra-centrifugation step provides the benefit of concentrating CAIV. This supports the use of a smaller delivered volume (0.1 mL per nostril rather than 0.25 mL per nostril, e.g., as might be used for frozen FluMist). Such reduced volume is more typical of nasally administered products and can increase consumer acceptance and reduce product losses due to swallowing or vaccine dripping out of the nose. Infected allantoic fluid harvest titers for CAIV have typically been between 8.3 and 9.5 $\log_{10} TCID_{50}/mL$, which is more than an order of magnitude above the target product concentration for frozen FluMist (7.3 $\log_{10} TCID_{50}/mL$, or 7.0 $\log_{10} TCID_{50}$ per dose). In the event that a very low titer strain is included in the annual vaccine recommendation, a liquid or RTS FluMist improves the chances of producing a full strength trivalent vaccine despite the increased virus concentration in the final product compared to frozen FluMist. Liquid or RTS FluMist is optionally formulated to a final concentration of 7.7 $\log_{10} TCID_{50}/mL$, which delivers the same amount of live virus per dose as frozen FluMist.

In one specific embodiment, a low titer influenza vaccine composition is provided whereby the viral titer is less than 7.3 $\log_{10} TCID_{50}/mL$, or less than 7.0 $\log_{10} TCID_{50}/mL$, or less than 6.0 $\log_{10} TCID_{50}/mL$, or less than 5.0 $\log_{10} TCID_{50}/mL$, or less than 4.0 $\log_{10} TCID_{50}/mL$, or less than 3.0 $\log_{10} TCID_{50}/mL$, or less than 2.0 $\log_{10} TCID_{50}/mL$. Such low titer influenza vaccine compositions may further comprise a pharmaceutically acceptable adjuvant, e.g., *E. coli* heat-labile toxin (or fragments thereof), pertussis toxin, aluminum. Other adjuvants include, but are not limited to aluminum phosphate, aluminum hydroxide, MPL™ (3-O-deacylated monophosphoryl lipid A; RIBI ImmunoChem Research, Inc., Hamilton, Mont., now Corixa), synthetic lipid A analogs such as 529 (Corixa), Stimulon™ QS-21 (Aquila Biopharmaceuticals, Framingham, Mass.), IL-12 (Genetics Institute, Cambridge, Mass.), synthetic polynucleotides such as oligonucleotides containing a CpG motif (U.S. Pat. No. 6,207,646 (28)), and cholera toxin (either in a wild-type or mutant form, for example, where the glutamic acid at amino acid position 29 is replaced by another amino acid, preferably a histidine, in accordance with published International Patent Application Number WO 00/18434).

In one specific embodiment, diafiltration may be used in the preparation of virus compositions of the invention. For instance, diafiltration may be used to concentrate the virus prior to formulation. Diafiltration may be used in addition to or instead of ultracentrifugation.

After an initial phase described later herein, cGMP production was initiated at the scale of 10,000 eggs per lot. A/Beijing/262/95 (H1N1), A/Sydney/05/97 (H3N2) and B/Ann Arbor/1/94 (B/harbin/7/94-like) purified monovalent CAIV bulks were manufactured to support subsequent clinical trials. The B/Ann Arbor strain is hereafter referred to as B/Harbin/7/94-like. For convenience, strain designations are often abbreviated (e.g., A/Beijing). The current application describes most heavily the process steps unique to the liquid FluMist, however, steps involved in both or common to both liquid and frozen FluMist are also described herein.

Methods for egg management and preparation of fresh virus harvest were essentially the same in various embodiments of the current invention (with the exception of automated inoculation and harvesting) for frozen FluMist as for liquid FluMist and those of skill in the art will be aware of similar or equivalent steps which are capable of use with the current invention. In the current invention, ultra-centrifugation was performed using a Hitachi CP40Y zonal centrifuge and an RP40CT Type D continuous-flow rotor (rotor volume=3.2 L). Virus harvest was first pooled, stabilized with sucrose phosphate glutamate (SPG) to facilitate filtration, then passed through a 5 micron polypropylene filter. The filtrate was then loaded onto a 10% to 60% sucrose gradient, banded for one hour at 40,000 rpm, and eluted into 100-ml fractions.

Fractions containing high hemagglutinin (HA) levels were pooled, diluted to 0.2M sucrose concentration, and then sterile filtered using a polyvinylidene fluoride (PVDF) 0.2 micron filter. The resulting bulk purified monovalent CAIV was frozen in 1 L bottles below –60 degrees C. and held for further processing.

Formulation and Filing

Initial formulation screening determined that the liquid phase stability of purified CAIV at refrigerated temperatures was suitable for an annual vaccine. Hydrolyzed animal gelatin added to the frozen FluMist stabilizer SPG provided the best stability results, with a least stable strain and lot from the CTM-1 campaign showing a loss of one log over 6.9 months. Further formulation development studies showed that the stability of liquid FluMist could be further improved by storing frozen just after manufacture, and thawing before final distribution. The stability of the worst-case strain was also improved by addition of arginine. While animal gelatins can raise concerns with regard to transmissible spongiform encephalopathies (TSE), available formulations lacking gelatin did not achieve the required stability in all embodiments. Thus, porcine gelatin was chosen for the some embodiments of liquid FluMist formulation due to its stabilizing properties and the fact that there are no reported occurrences of TSE in pigs. The harsh chemical processing steps used in collagen hydrolysis are also thought to cause inactivation of prion-sized proteins.

Frozen, purified monovalent bulk CAIV was shipped and trivalent vaccine was produced under cGMP to support clinical testing of liquid FluMist. A total of six fills were performed. Blending was performed at small scale using a 4-liter glass aspirator flask, and 0.5 mL Becton Dickinson (BD) Hypack SCF (sterile, clean, ready to fill) glass sprayers were filled using an INOVA automated filler/stopperer and associated equipment. The manufacture of filled trivalent liquid FluMist is described in more detail below.

Specific Formulation Embodiments of the Invention

In one embodiment, the vaccine formulations of the invention comprise one or more of the following in the final formulations: sucrose: 6-8% weight/volume (w/v); arginine monohydrochloride 1-2% w/v; glutamic acid, monosodium monohydrate 0.05-0.1% w/v; gelatin hydrolysate, porcine Type A (or other sources) 0.5-2% w/v; potassium phosphate dibasic 1-2%; and potassium phosphate monobasic 0.25-1% w/v.

In one specific embodiment, vaccine formulations comprise one or more of the following: sucrose: 6.84% weight/volume (w/v); arginine monohydrochloride 1.21% w/v; glutamic acid, monosodium monohydrate 0.094 w/v; gelatin hydrolysate, porcine Type A (or other sources) 1% w/v; potassium phosphate dibasic 1.13%; and potassium phosphate monobasic 0.48% w/v. In another specific embodiment, vaccine formulations comprise all of the following: sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v.

In another specific embodiment, vaccine formulations comprise all of the following (within 10% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v.

In another specific embodiment, vaccine formulations comprise all of the following (within 10% variation of one or more component): sucrose: 6.84% weight/volume (w/v); arginine monohydrochloride 1.21% w/v; gelatin hydrolysate, porcine Type A (or other sources) 1% w/v. In such embodiments, formulation are in buffer (e.g., a potassium phosphate buffer (pH 7.0-7.2)).

In another specific embodiment, vaccine formulations comprise all of the following (within 20% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v.

In another specific embodiment, vaccine formulations comprise all of the following (within 30% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v.

In another specific embodiment, vaccine formulations comprise all of the following (within 40% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v.

In another specific embodiment, vaccine formulations comprise all of the following (within 1% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v.

In another specific embodiment, vaccine formulations comprise all of the following (within 3% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v.

In a specific embodiment, formulations of the invention may contain, e.g., potassium phosphate (e.g., at least 50 mM, or at least 100 mM, or at least 200 mM, or at least 250 mM) as a buffer or alternatively, histidine (e.g., at least 50 mM, or at least 100 mM, or at least 200 mM, or at least 250 mM).

Other Specific Embodiments of the Invention, e.g., Dosing, Potency

In another specific embodiment, methods of administering the vaccine formulations of the invention intranasally are included. For instance, vaccine formulations of the invention may be administered intranasally in final doses of 0.5 mL/dose; 0.75 mL/does; 0.1 mL/does; 0.15 mL/does; 0.2 mL/dose; 0.25 mL/dose; 0.5-0.1 mL/dose; 0.5 mL-2 mL/dose; or 0.5-2.5 mL/dose.

In one embodiment, vaccine formulations of the invention comprise approximately $10^7$ fluorescent focus units (FFU) or $10^7$ $TCID_{50}$ of each of three different reassortant strains of influenza. In another specific embodiment, vaccine formulations of the invention comprise a potency of 7.0 (+/-0.5) log 10 FFU/dose (or $TCID_{50}$/dose) for each strain of influenza virus. In another specific embodiment, vaccine formulations of the invention comprise a potency of 7.0 (+/-0.5) log 10 FFU/dose (or $TCID_{50}$/dose) for at least one strain of influenza virus. In another specific embodiment, vaccine formulations of the invention have a potency of at least (or equal to) 6.0 log 10 FFU/dose, 6.5 log 10 FFU/dose, 6.7 log 10 FFU/dose 6.7 log 10 FFU/dose, 6.8 log 10 FFU/dose, 6.9 log 10 FFU/dose, 7.0 log 10 FFU/dose, 7.1 log 10 FFU/dose, 7.2 log 10 FFU/dose, 7.3 log 10 FFU/dose, 7.4 log 10 FFU/dose, 7.5 log 10 FFU/dose, 7.6 log 10 FFU/dose, 7.7 log 10 FFU/dose, 7.8 log 10 FFU/dose, 7.9 log 10 FFU/dose, 8.1 log 10 FFU/dose, 8.5 log 10 FFU/dose or 8.8 log 10 FFU/dose.

Potency may be measured by $TCID_{50}$ instead of FFU in each embodiment of the invention. A Fluorescent Focus Assay (FFA) is a direct measure of the infectivity in the vaccine while $TCID_{50}$ is an indirect measure which measures the ability of productive replication in MDCK or other cells.

In another specific embodiment, vaccine formulations of the invention have a potency of between 6.5-7.5 log 10 FFU per dose (e.g., per 0.2 mL dose).

In another specific embodiment, vaccine formulations of the invention have a potency of at least (or equal to) 7.0 $\log_{10}$ $TCID_{50}$ per dose, or at least 6-8 $TCID_{50}$ per dose, or at least 6.4 $TCID_{50}$ per dose, or at least 6.6 $\log_{10}$ $TCID_{50}$ per dose.

In one embodiment, vaccine formulations of the invention have pH of 6.7-7.7, or 6.6, or 6.7, or 6.8, or 6.9, or 7.0, or 7.1, or 7.2, or 7.3, or 7.4, or 7.5, or 7.6, or 7.7.

In another specific embodiment, the vaccine formulations of the invention have no greater than 60 EU/mL of endotoxin, or have no greater than 200 EU/mL of endotoxin. For instance, the vaccine formulations of the invention have less than or equal to 5 EU/mL of endotoxin. In another specific embodiment, the vaccine formulations of the invention have less than or equal to 1.0 EU/7.0 log 10 FFU.

In another specific embodiment, the vaccine formulations of the invention are free of one or more (or all) of the following: mycoplasma, retrovirus, avian leucosis virus, and mycobacterium (e.g., *M. tuberculosis*). Methods of the producing such formulations of the invention may comprise the step(s) of testing for such impurities.

In another specific embodiment, the vaccine formulations of the invention may contain influenza viruses having HA and NA genes from three different viruses as in FluMist.

In one specific embodiment, formulations of the invention comprise one or more (or all) of the following per dose (e.g., per 0.2 mL dose): sucrose (13.68 mg), dibasic potassium phosphate (2.26 mg), monobasic potassium phosphate (0.96 mg), gelatin hydrolysate (2.0 mg), arginine hydrochloride (2.42 mg), and monosodium glutamate (0.188 mg).

In one specific embodiment, formulations of the invention comprise one or more (or all) of the following per dose (e.g., per 0.2 mL dose): sucrose (13.68 mg), potassium phosphate (100 mM), gelatin hydrolysate (2.0 mg), arginine hydrochloride (2.42 mg), and monosodium glutamate (0.188 mg).

In another specific embodiment, formulations of the invention comprise one or more (or all) of the following (plus or minus 10%, or 20% or 30% or 40%) per dose: sucrose (13.68 mg), dibasic potassium phosphate (2.26 mg), monobasic potassium phosphate (0.96 mg), gelatin hydrolysate (2.0 mg), arginine hydrochloride (2.42 mg), and monosodium glutamate (0.188 mg).

In another specific embodiment, formulations of the invention comprise one or more (or all) of the following (plus or minus 10%, or 20% or 30% or 40%) per dose: sucrose (13.68 mg), potassium phosphate (100 mM), gelatin hydrolysate (2.0 mg), arginine hydrochloride (2.42 mg), and monosodium glutamate (0.188 mg).

In another specific embodiment, formulations of the invention comprise an influenza virus comprising the genetic backbone of one or more of the following influenza viruses: A/Ann Arbor/6/60 (A/AA/6/60) B/Ann Arbor/1/66 virus, the FluMist MDV-A (ca A/Ann Arbor/6/60), the FluMist MDV-B (ca B/Ann Arbor/1/66), A/Leningrad/17 donor strain backbone, and PR8.

In another specific embodiment, the vaccine formulations of the invention comprise an influenza virus comprising an HA and an NA polypeptide sequence (or at least 90% identical or at least 95% identical to such sequences) from one or more of the following: B/Yamanashi; A/New Caledonia; A/Sydney; A/Panama; B/Johannesburg; B/Victoria; B/Hong Kong; A/Shandong/9/93; A/Johannesburg/33/94; A/Wuhan/395/95; A/Sydney/05/97; A/Panama/2007/99; A/Wyoming/03/2003; A/Texas/36/91; A/Shenzhen/227/95; A/Beijing/262/95; A/New Caledonia/20/99; B/Ann Arbor/1/94; B/Yamanashi/166/98; B_Johannesburg_5_99; B/Victoria/504/2000; B/Hong Kong/330/01; B_Brisbane_32_2002; B/Jilin/20/03; an H1N1 influenza A virus, an H3N2 influenza A virus, H9N2 influenza A virus, an H5N1 influenza A virus; an influenza B virus; and a pandemic influenza strain (either designated by WHO or not circulating in the human population). See, e.g., US 20050042229.

In another specific embodiment, the vaccine formulations of the invention are sterile.

Description of Representative Steps in Vaccine Production

For ease in discussion and description, the various steps of vaccine composition production in general, can be thought of as comprising or falling into four broad groups (roughly similar to the presentation outlined previously above). The first group comprises such aspects as co-infection, reassortment, selection of reassortants, and cloning of reassortants. The second group comprises such aspects as purification and expansion of reassortants. The third group comprises further expansion of reassortants in eggs, along with harvesting and purification of such harvested virus solutions. The fourth group comprises stabilization of harvested virus solutions and potency/sterility assays of the virus solutions. It is to be understood, however, that division of the aspects of the invention into the above four general categories is solely for explanatory/organizational purposes and no inference of interdependence of steps, etc. should be made. Again, it will be appreciated that other steps (both similar and different) are optionally used with the methods and compositions of the invention (e.g., the methods and compositions for RTS vaccine compositions).

As mentioned above, for ease in discussion and description, the various steps of vaccine production can be thought of as comprising four broad groups. The first group comprises such aspects as co-infection, reassortment, selection of reassortants, and cloning of reassortants.

Group 1

The aspects of vaccine composition production which are broadly classified herein as belonging to Group 1, comprise methods and compositions related to optimization of co-infection of cell culture lines, e.g., with a master donor virus and one or more wild-type viruses in order to produce specifically desired reasserted viruses; selection of appropriate reassorted viruses; and cloning of the selected reassorted viruses. Reassortment of influenza virus strains is well known to those of skill in the art. Reassortment of both influenza A virus and influenza B virus has been used both in cell culture and in eggs to produce reassorted virus strains. See, e.g., Tannock et al., *Preparation and characterization of attenuated cold-adapted influenza A reassortants derived from the A/Leningrad/134/17/57 donor strain, Vaccine* (2002) 20:2082-2090. Reassortment of influenza strains has also been shown with plasmid constructs. See, e.g., U.S. patent application Nos. 60/375,675 filed Apr. 26, 2002, PCT/US03/12728 filed Apr. 25, 2003 and U.S. application Ser. No. 10/423,828, filed Apr. 25, 2003, PCT/US05/017734, filed May 20, 2005; and US20050186563.

Reassortment, in brief, generally comprises mixing (e.g., in eggs or cell culture) of gene segments from different viruses. For example, the typical 8 segments of influenza B virus strains can be mixed between, e.g., a wild-type strain having an epitope of interest and a "donor" strain, e.g., comprising a cold-adapted strain. Reassortment between the two virus types can produce, inter alia, viruses comprising the wild-type epitope strain for one segment, and the cold-adapted strain for the other segments. Unfortunately, to create the desired reassortants, sometimes large numbers of reassortments need to be done. After being reasserted, the viruses can also be selected (e.g., to find the desired reassortants). The desired reassortants can then be cloned (e.g., expanded in number).

Traditional optimization, selection, and cloning of desired reassortants for influenza B virus, typically occurs by co-infection of virus strains into a cell culture (e.g., CEK cells) followed by selection with appropriate antibodies, e.g., against material from one of the parent virus, (usually done in eggs), and cloning or expanding of virus, etc. which is typically done in cell culture. However, such traditional reassortment presents drawbacks in that thousands of reassortments are needed to create the desired segment mix. When such reassortments are done, it is apparent that truly random reassortments are not the end result. In other words, pressures that bias the process exist in the systems. For influenza A strains, however, such processes do not appear to have such bias. For A strains, co-infection of strains (typically into cell culture such as CEK cells) is followed by selection and cloning at the same time, again, typically in cell culture.

Optimization of Reassortment

Various embodiments utilizing the steps in Group 1 can optimize the reassortment process in order to reduce the number of reassortments needed (and thus increase the throughput/stability of the vaccine production process), etc. The steps utilizing such optimization techniques are typically embodied with reassortment of influenza B strains and are typically done in cell culture, e.g., CEK cells. See, e.g., U.S. patent application Ser. Nos. 10/788,236 and PCT/US04/05697 both filed Feb. 25, 2004, which are incorporated by reference in their entirety for all purposes, both within this section and throughout the specification.

Other methods of reassortment of influenza virus can optionally mix dilutions of a master donor virus (MDV) and a wild-type virus, e.g., a 1:5 dilution of each no matter the concentration of the respective solutions, which are then incubated for 24 and 48 hours at 25° C. and 33° C. While such an approach is often acceptable for influenza A strains, influenza B strains do not typically give positive results with such protocol. For example, to achieve the proper 6:2 assortment (i.e., 6 genes from the MDV and 2 genes, NA and HA from the wild-type virus) thousands of reassortments must often be done.

Selection and Cloning of Reassortments

The steps in Group 1 also comprise selection of reassorted influenza viruses. Reassorted influenza A strains are capable of selection in either cell culture (e.g., CEK cells) or in eggs. However, reasserted influenza B strains present problems when reasserted in cell culture (e.g., when selected for in CEK cells). It is believed that CEK cells interfere with the M gene in influenza B strains, thus reducing the overall production. Various methods of vaccine composition production, see, e.g., See, e.g., U.S. patent application Ser. Nos. 10/788,236 and PCT/US04/05697 both filed Feb. 25, 2004, utilize different steps for virus reassortment, e.g., selection, such steps can optionally be used to create virus for the vaccine compositions.

Characterization of Reassortments

Yet other methods of virus/vaccine production utilize applications of a high throughput single strand conformation polymorphism/capillary electrophoresis (SSCP/CE) assay to determine the gene constellation of influenza viruses used herein. Influenza viruses contain 8 gene segments and, as described above, co-infection of a single cell with two different influenza strains can produce reassortant viruses with novel gene constellations distinct from either parent. Thus, some methods can use a SSCP/CE assay to rapidly determine the gene segment constellation of a large number of influenza virus samples. The influenza viral gene segments are optionally amplified by RT-PCR using fluorescent-labeled primers specific for each of the eight segments. See, also, Arvin et al. (2000) Clin. Micro. J38(2):839-845 which is incorporated herein by reference for all purposes.

Prevention of Bacterial Contamination

Some methods of virus/vaccine production can comprise steps to detect and/or prevent/detect microbial contamination of eggs in which influenza virus is produced. The microbial detection strategies of the invention are useful for rapid/high throughput microbial detection and, thus, as with many other steps, are useful for increasing throughput and optionally stability in virus/vaccine production.

Many current influenza vaccine production strategies, which can optionally be used with the invention herein, use as a component, the traditional method for influenza virus expansion in specific-pathogen-free fertile chicken eggs. Possible microbial contamination can occur in several points in the production of virus in eggs. Unfortunately, the chicken eggs may have some microorganisms outside of their shells as part of their natural flora. It is also possible to have microorganisms enclosed within the shell of the egg during the development of the chicken embryo. Fertilized chicken eggs are incubated at 37° C. in high humidity for development of the embryo, which constitutes prime incubation conditions for many types of microbial contaminants as well. Another possible time of microbial contamination occurs when the shell is punctured to inoculate the egg. Even though prior to virus inoculation, the eggs are often sprayed with alcohol, there is still opportunity for microorganisms to enter into the egg.

After expansion of viruses for 2 to 3 days in the eggs, the top of the eggshell is typically removed for manual harvesting of the allantoic fluid containing virus within the egg. See, above. This harvesting is another point where microbial contamination may originate. Unfortunately eggs with such contaminating bioburden may escape detection, necessitating pooling into multiple bottles to minimize the rejection of the entire lot due to a failed MPA test. Since three influenza strains are typically used in vaccine production, blending of the three strains is required for the final bulk. In-process MPA (microbiological purity assay) testing is performed, e.g., at virus harvest prior to use in the blending and filling to ensure microbial-free product.

After incubation, the "traditional" method of candling is used to identify infertile and dead eggs that are possibly dead due to natural causes or to microbial contamination (i.e., dead eggs may occur due to infectivity of the virus and/or expansion of microorganisms, both of which require detection and removal of such eggs). Candling comprises, e.g., the process of holding an egg in front of a light source in a darkened room to enable visualization of the developing embryo. Dead eggs are excluded from virus inoculation.

As can be seen from the above points, detection of microbial contamination can be needed at multiple steps during the manufacture of influenza vaccine. There is a need to eliminate or reduce avian and environmental microbes and a need to eliminate or reduce introduction of environmental and human microbes. Current methods for detection of contaminating microorganisms include, e.g., compendial methods (MPA and Bioburden). Current methods can include, e.g., egg candling during egg pre/post inoculation (which is typically done manually at a rate of about 500 eggs/hour/person); MPA and BioBurden tests which are typically manual and take about 14 days for MPA and about 3 days for BioBurden (which are done during virus harvest); mycoplasma testing; which is typically done manually and takes about 28 days (done during virus harvest); and mycobacterium testing which is typically manual and takes about 56 days (done during virus harvest). Again, see, e.g., U.S. patent application Ser. Nos. 10/788,236 and PCT/US04/05697 both filed Feb. 25, 2004, for descriptions of various techniques capable of use with the current invention.

Group 2

Aspects of virus/vaccine production that fall into Group 2 include further purification and virus expansion, etc. After the process of correct reassortment and cloning of reassortants (i.e., the 6:2 viruses), such reassorted virus particles are further purified in embryonated hen eggs and the correct clones are expanded in quantity (again through growth in hen eggs) to generate a master virus strain (MVS) or master virus seed, which, in turn, is further expanded to generate a master working virus strain (MWVS) or manufacturer's working virus seed. Many aspects of purification of virus particles from eggs and use of such purified virus to inoculate more eggs in order to expand the quantity of virus particles are well known to those skilled in the art. Many such techniques are common in the current production of virus particles and have been used for at least 40 years. See, e.g., Reimer, et al. *Influenza virus purification with the zonal ultracentrifuge*, Science 1966, 152:1379-81. Purification protocols can involve, e.g., ultracentrifugation in sucrose gradients (e.g., 10-40% sucrose), etc. Also, as noted herein, other procedures, etc. listed in other Groups are also optionally present within Group 2, e.g., prevention of microbial contamination, etc.

Group 3

Aspects of virus/vaccine production that fall under the heading of Group 3 include, e.g., conditioning of the embryonated eggs (e.g., specific handling and environmental conditions involved in the incubation of virus infected eggs) and the harvesting and clarification of influenza virus from the allantoic fluid of the eggs.

For example, conditioning, washing, candling, and incubating eggs which contain the reasserted virus to be used in a vaccine; inoculation, sealing, etc. of such eggs; candling of such eggs; harvesting of the virus solution (e.g. the allantoic fluid or Viral Harvest (VH)) from the eggs; and clarification of the virus solution can all fall within such category. Again, it should be noted that several techniques applicable to the steps in Groups 2 are equally applicable to the steps in Group 3 (e.g., candling, etc.). Several aspects of virus/vaccine production that comprise Groups 3 are well known to those skilled in the art. Various aspects of candling of eggs in virus production, as well as inoculation of eggs with viruses and washing, incubating, etc. of such eggs are well known techniques in the production of virus/vaccines in eggs. Of course, it will be appreciated that such well-known techniques are used in conjunction with the unique and innovate aspects of the current invention. See, e.g., U.S. patent application Ser. Nos. 10/788,236 and PCT/US04/05697 both filed Feb. 25, 2004, give further steps such as rocking, etc. that can also be used with the methods and compositions of the current invention. Other similar steps can include specific filtering and warming of compositions, again, see, the same.

Filtering and Warming

The current invention involves aspects of ultra-centrifugation, see above, which can fall into the current grouping. In addition, U.S. patent application Ser. Nos. 10/788,236 and PCT/US04/05697 both filed Feb. 25, 2004 also give other filtering and warming steps that can optionally be used with the methods and compositions of the current invention. As described, the FluMist™ manufacturing process can use embryonated chicken eggs to generate master virus seeds (MVS), manufacturer's working virus seeds (MWVS) and virus harvests (VH). The seeds and viral harvest may contain bioburden (typically bacterial contamination), which would cause the seed or bulk virus product lots to be rejected in the vaccine production process. Of course, it will be appreciated that specific listing or description of particular product types used, sizes, etc., is not to be considered limiting on the current invention unless specifically stated to be so.

Group 4

Group 4 of the aspects of vaccine formulation/composition production comprises, e.g., steps primarily concerned with stabilization (e.g., through addition of components, alterations in buffer/NAF ratios, etc.) and assays of potency/sterility of virus containing solutions. The description of the current invention above, gives various aspects which can optionally be grouped within the current category. See, above.

In some embodiments, the final viral solutions/vaccines comprising live viruses are stable in liquid form for a period of time sufficient to allow storage "in the field" (e.g., on sale and commercialization when refrigerated at 2-8° C., 4° C., 5° C., etc.) throughout an influenza vaccination season (e.g., typically from about September through March in the northern hemisphere). Thus, the virus/vaccine compositions are desired to retain their potency or to lose their potency at an acceptable rate over the storage period. In other embodiments, such solutions/vaccines are stable in liquid form at from about 2° C. to about 8° C., e.g., refrigerator temperature. For example, if a 0.3 log potency loss was acceptable and the storage period were 9 months, then an 0.05 log/month decrease in potency would be acceptable. As another example, if a loss of up to 0.75 log were allowed, a rate of less than or equal to 0.09 log/month would be sufficient to allow stability of materials stored continuously at refrigerator temperature (e.g., 4° C.). In other embodiments, such solutions/vaccines are stable in liquid form when stored at from about 2° C. to about 8° C. The stability of the composition can comprise between about 1 day and 2 years, between about 10 days and about 2 years, between about 20 days and about 2 years, between about 1 month and about 2 years, between about 2 months and about 2 years, between about 3 months and about 2 years, between about 4 months and about 2 years, between about 5 months and about 2 years, between about 6 months and about 2 years, between about 7 months and about 2 years, between about 8 months and about 2 years, between about 9 months and about 2 years, between about 10 months and about 2 years, between about 11 months and about 2 years, between about 12 months and about 2 years, between about 13 months and about 2 years, between about 14 months and about 2 year, between about 15 months and about 2 years, between about 16 months and about 2 years, between about 17 months and about 2 years, between about 18 months and about 2 years, between about 19 months and about 2 years, between about 20 months and about 2 years, between about 21 months and about 2 years, between about 22 months and about 2 years, between about 23 months and about 2 years, or greater than about 2 years.

One may test the stability of a formulation of the invention by a number of methods. For instance, one may first incubate a formulation at freezing temperatures (e.g., −25 or −70° C. (+/−10, 20, 30, or 40° C.) and then store (or "incubate") the formulation at 4-8° C. for a length of time. Alternatively, one may test the stability of a formulation of the invention by simply storing (or "incubating") the formulation at 4-8° C. for a length of time. Potency could be measured by a number of methods as described herein or otherwise known.

Concentration/Diafiltration of Virus Harvests

In some methods of vaccine composition production, virus harvests are optionally concentrated using an appropriate column. See, U.S. patent application Ser. Nos. 10/788,236 and PCT/US04/05697 both filed Feb. 25, 2004.

Stabilizers/Buffers

Vaccine composition production can also optionally include various dilutions of NAF (typically unfractionated NAF) comprising the virus of interest and combinations of, e.g., sucrose, arginine, gelatin, EDTA, etc. See, e.g., U.S. patent application Ser. Nos. 10/788,236 and PCT/US04/05697, for examples of various combinations possible in different vaccine formulations. Such methods and compositions are preferably stable, e.g., do not show unacceptable losses in potency, e.g., a potency loss of between 0.5-1.0 logs, or less than 0.5 logs, or less than 1.0 logs, over selected time periods (typically at least 6 months, at least 9 months, at least 12 months, at least 15 months, at least 18 months, at least 24 months, etc.) at desired temperatures (e.g., typically 4° C., 5° C., 8° C., from about 2° C. to about 8° C. or greater than 2° C., etc.).

In some formulations, compositions can comprise a stabilizer of, e.g., arginine (of pH from about 7.0 to about 7.2), either in combination with, or in place of gelatin or gelatin related and/or derived products (e.g., gelatin hydrosylate). See U.S. patent application Ser. Nos. 10/788,236 and PCT/US04/05697. Also, in many virus solutions/vaccine solutions a base solution of SPG (sucrose, potassium phosphate and monosodium glutamate) is optionally utilized.

U.S. patent application Ser. Nos. 10/788,236 and PCT/US04/05697 both filed Feb. 25, 2004 give other/additional methods of virus/vaccine composition stabilization, e.g., NAF level manipulation, etc.

Definitions

Unless defined otherwise, all scientific and technical terms are understood to have the same meaning as commonly used in the art to which they pertain. For the purpose of the present invention the following terms are defined below.

The terms "nucleic acid," "polynucleotide," "polynucleotide sequence" and "nucleic acid sequence" refer to single-stranded or double-stranded deoxyribonucleotide or ribonucleotide polymers, or chimeras or analogues thereof. As used herein, the term optionally includes polymers of analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence optionally encompasses complementary sequences, in addition to the sequence explicitly indicated.

The term "gene" is used broadly to refer to any nucleic acid associated with a biological function. Thus, genes include coding sequences and/or the regulatory sequences required for their expression. The term "gene" applies to a specific genomic sequence, as well as to a cDNA or an mRNA encoded by that genomic sequence.

Genes also include non-expressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "tissue specific" promoter or enhancer is one that regulates transcription in a specific tissue type or cell type, or types.

The term "vector" refers to the means by which a nucleic acid can be propagated and/or transferred between organisms, cells, or cellular components. Vectors include plasmids, viruses, bacteriophage, pro-viruses, phagemids, transposons, and artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not autonomously replicating. Most commonly, but not necessarily exclusively, the vectors of herein refer to plasmids.

An "expression vector" is a vector, such as a plasmid that is capable of promoting expression, as well as replication of, a nucleic acid incorporated therein. Typically, the nucleic acid to be expressed is "operably linked" to a promoter and/or enhancer, and is subject to transcription regulatory control by the promoter and/or enhancer.

A "bidirectional expression vector" is characterized by two alternative promoters oriented in the opposite direction relative to a nucleic acid situated between the two promoters, such that expression can be initiated in both orientations resulting in, e.g., transcription of both plus (+) or sense strand, and negative (−) or antisense strand RNAs.

In the context herein, the term "isolated" refers to a biological material, such as a nucleic acid or a protein, which is substantially free from components that normally accompany or interact with it in its naturally occurring environment. The isolated material optionally comprises material not found with the material in its natural environment, e.g., a cell. For example, if the material is in its natural environment, such as a cell, the material has been placed at a location in the cell (e.g., genome or genetic element) not native to a material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids.

The term "recombinant" indicates that the material (e.g., a nucleic acid or protein) has been artificially or synthetically (non-naturally) altered. The alteration can be performed on the material within, or removed from, its natural environment or state. Specifically, when referring to a virus, e.g., an influenza virus, is recombinant when it is produced by the expression of a recombinant nucleic acid.

The term "reassortant," when referring to a virus, indicates that the virus includes genetic and/or polypeptide components derived from more than one parental viral strain or source. For example, a 7:1 reassortant includes 7 viral genomic segments (or gene segments) derived from a first parental virus, and a single complementary viral genomic segment, e.g., encoding hemagglutinin or neuramimidase, from a second parental virus. A 6:2 reassortant includes 6 genomic segments, most commonly the 6 internal genes from a first parental virus, and two complementary segments, e.g., hemagglutinin and neuramimidase, from a different parental virus.

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such methods as "infection," "transfection," "transformation," and "transduction." In the context of the invention, a variety of methods can be employed to introduce nucleic acids into prokaryotic cells, including electroporation, calcium phosphate precipitation, lipid mediated transfection (lipofection), etc.

The term "host cell" means a cell that contains a heterologous nucleic acid, such as a vector, and supports the replication and/or expression of the nucleic acid. Host cells can be prokaryotic cells such as E. coli, or eukaryotic cells such as yeast, insect, amphibian, avian or mammalian cells, including human cells. Exemplary host cells in the context of the invention include Vero (African green monkey kidney) cells, BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), and COS cells (e.g., COS1, COS7 cells).

Influenza Virus

The compositions and methods herein are primarily concerned with production of influenza viruses for vaccines. Influenza viruses are made up of an internal ribonucleoprotein core containing a segmented single-stranded RNA genome and an outer lipoprotein envelope lined by a matrix protein. Influenza A and influenza B viruses each contain eight segments of single stranded negative sense RNA. The influenza A genome encodes eleven polypeptides. Segments 1-3 encode three polypeptides, making up a RNA-dependent RNA polymerase. Segment 1 encodes the polymerase complex protein PB2. The remaining polymerase proteins PB1 and PA are encoded by segment 2 and segment 3, respectively. In addition, segment 1 of some influenza strains encodes a small protein, PB1-F2, produced from an alternative reading frame within the PB1 coding region. Segment 4 encodes the hemagglutinin (HA) surface glycoprotein involved in cell attachment and entry during infection. Segment 5 encodes the nucleocapsid nucleoprotein (NP) polypeptide, the major structural component associated with viral RNA. Segment 6 encodes a neuramimidase (NA) envelope glycoprotein. Segment 7 encodes two matrix proteins, designated M1 and M2, which are translated from differentially spliced mRNAs. Segment 8 encodes NS1 and NS2, two nonstructural proteins, which are translated from alternatively spliced mRNA variants.

The eight genome segments of influenza B encode 11 proteins. The three largest genes code for components of the RNA polymerase, PB 1, PB2 and PA. Segment 4 encodes the HA protein. Segment 5 encodes NP. Segment 6 encodes the NA protein and the NB protein. Both proteins, NB and NA, are translated from overlapping reading frames of a biscistronic mRNA. Segment 7 of influenza B also encodes two proteins: M1 and M2. The smallest segment encodes two products, NS1 which is translated from the full length RNA, and NS2 which is translated from a spliced mRNA variant.

Influenza Virus Vaccine

Historically, influenza virus vaccines have primarily been produced in embryonated hen eggs using strains of virus selected based on empirical predictions of relevant strains. More recently, reassortant viruses have been produced that incorporate selected hemagglutinin and neuramimidase antigens in the context of an approved attenuated, temperature sensitive master strain. Following culture of the virus through multiple passages in hen eggs, influenza viruses are recovered and, optionally, inactivated, e.g., using formaldehyde and/or β-propiolactone (or alternatively used in live attenuated vaccines).

However, production of influenza vaccine in this manner has several significant concerns. For example, contaminants remaining from the hen eggs can be highly antigenic and/or pyrogenic, and can frequently result in significant side effects upon administration. Thus, another method involves replacement of some percentage of egg components with animal free media. More importantly, virus strains designated for vaccine production must be selected and distributed, typically months in advance of the next flu season to allow time for production and inactivation of influenza vaccine. Again, any improvements in stability in storage time and/or of storage at a more convenient temperature (e.g., refrigerator temperature of about 2-8° C., e.g., as through use of the methods and compositions of the current invention), are thus quite desirable.

Attempts at producing recombinant and reassortant vaccines in cell culture have been hampered by the inability of some of the strains approved for vaccine production to grow efficiently under standard cell culture conditions. Thus, prior work by the inventor and his coworkers provided a vector system, and methods for producing recombinant and reassortant viruses in culture, thus, making it possible to rapidly produce vaccines corresponding to one or many selected antigenic strains of virus. See, e.g., U.S. patent application Nos. 60/375,675 filed Apr. 26, 2002, PCT/US03/12728 filed Apr. 25, 2003 and U.S. Ser. No. 10/423,828 filed Apr. 25, 2003, PCT/US05/017734 filed May 20, 2005. Of course, such reassortments are optionally further amplified in hen eggs. Typically, the cultures are maintained in a system, such as a cell culture incubator, under controlled humidity and $CO_2$, at constant temperature using a temperature regulator, such as a thermostat to insure that the temperature does not exceed 35° C. Such pioneering work, as well as other vaccine production, can be further optimized through use of the current invention in whole or part.

Reassortant influenza viruses can be readily obtained by introducing a subset of vectors corresponding to genomic segments of a master influenza virus, in combination with complementary segments derived from strains of interest (e.g., antigenic variants of interest). Typically, the master strains are selected on the basis of desirable properties relevant to vaccine administration. For example, for vaccine production, e.g., for production of a live attenuated vaccine, the master donor virus strain may be selected for an attenuated phenotype, cold adaptation and/or temperature sensitivity.

FluMist®

As mentioned previously, numerous examples and types of influenza vaccine exist. An exemplary influenza vaccine is FluMist which is a live, attenuated vaccine that protects children and adults from influenza illness (Belshe et al. (1998) *The efficacy of live attenuated, cold-adapted, trivalent, intranasal influenza virus vaccine in children N. Engl. J. Med.* 338:1405-12; Nichol et al. (1999) *Effectiveness of live, attenuated intranasal influenza virus vaccine in healthy, working adults: a randomized controlled trial JAMA* 282: 137-44). In typical embodiments, the methods and compositions of the current invention are preferably adapted to, or used with, production of FluMist vaccine. However, it will be appreciated by those skilled in the art that the steps/compositions herein are also adaptable to production of similar or even different viral vaccines and their compositions.

FluMist™ vaccine strains contain, e.g., HA and NA gene segments derived from the wild-type strains to which the vaccine is addressed along with six gene segments, PB1, PB2, PA, NP, M and NS, from a common master donor virus (MDV). The MDV for influenza A strains of FluMist (MDV-A), was created by serial passage of the wild-type A/Ann Arbor/6/60 (A/AA6/60) strain in primary chicken kidney tissue culture at successively lower temperatures (Maassab (1967) *Adaptation and growth characteristics of influenza virus at 25 degrees C. Nature* 213:612-4). MDV-A replicates efficiently at 25° C. (ca, cold adapted), but its growth is restricted at 38 and 39° C. (ts, temperature sensitive). Additionally, this virus does not replicate in the lungs of infected ferrets (att, attenuation). The ts phenotype is believed to contribute to the attenuation of the vaccine in humans by restricting its replication in all but the coolest regions of the respiratory tract. The stability of this property has been demonstrated in animal models and clinical studies. In contrast to the ts phenotype of influenza strains created by chemical mutagenesis, the ts property of MDV-A does not revert following passage through infected hamsters or in shed isolates from children (for a recent review, see Murphy & Coelingh (2002) *Principles underlying the development and use of live attenuated cold-adapted influenza A and B virus vaccines Viral Immunol.* 15:295-323).

Clinical studies in over 20,000 adults and children involving 12 separate 6:2 reassortant strains have shown that these vaccines are attenuated, safe and efficacious (Belshe et al. (1998) *The efficacy of live attenuated, cold-adapted, trivalent, intranasal influenza virus vaccine in children N. Engl. J. Med.* 338:1405-12; Boyce et al. (2000) *Safety and immunogenicity of adjuvanted and unadjuvanted subunit influenza vaccines administered intranasally to healthy adults Vaccine* 19:217-26; Edwards et al. (1994) *A randomized controlled trial of cold adapted and inactivated vaccines for the prevention of influenza A disease J. Infect. Dis.* 169:68-76; Nichol et al. (1999) *Effectiveness of live, attenuated intranasal influenza virus vaccine in healthy, working adults: a randomized controlled trial JAMA* 282:137-44). Reassortants carrying the six internal genes of MDV-A and the two HA and NA gene segments of a wild-type virus (i.e., a 6:2 reassortant) consistently maintain ca, ts and att phenotypes (Maassab et al. (1982) *Evaluation of a cold-recombinant influenza virus vaccine in ferrets J. Infect. Dis.* 146:780-900). Production of such reasserted virus using B strains of influenza is more difficult, however.

Recent work, see, see, e.g., U.S. patent application Nos. 60/375,675 filed Apr. 26, 2002, PCT/US03/12728 filed Apr. 25, 2003 and U.S. Ser. No. 10/423,828 filed Apr. 25, 2003, PCT/US05/017734 filed May 20, 2005 has shown an eight plasmid system for the generation of influenza B virus entirely from cloned cDNA, and methods for the production of attenuated live influenza A and B virus suitable for vaccine formulations, such as live virus vaccine formulations useful for intranasal administration.

The system and methods described previously are useful for the rapid production in cell culture of recombinant and reassortant influenza A and B viruses, including viruses suitable for use as vaccines, including live attenuated vaccines, such as vaccines suitable for intranasal administration such as FluMist®. The methods of the current invention herein, are optionally used in conjunction with or in combination with such previous work involving, e.g., reasserted influenza viruses for vaccine production to produce viruses for vaccines in a more stable, consistent and productive manner.

Cell Culture

As previously stated, influenza virus optionally can be grown in cell culture. Typically, propagation of the virus is accomplished in the media compositions in which the host cell is commonly cultured. Suitable host cells for the replication of influenza virus include, e.g., Vero cells, BHK cells, MDCK cells, 293 cells and COS cells, including 293T cells, COS7 cells. Commonly, co-cultures including two of the above cell lines, e.g., MDCK cells and either 293T or COS cells are employed at a ratio, e.g., of 1:1, to improve replication efficiency. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

Procedures for maintaining mammalian cells in culture have been extensively reported, and are well known to those of skill in the art. General protocols are provided, e.g., in Freshney (1983) Culture of Animal Cells: Manual of Basic Technique, Alan R. Liss, New York; Paul (1975) Cell and Tissue Culture, 5$^{th}$ ed., Livingston, Edinburgh; Adams (1980) Laboratory Techniques in Biochemistry and Molecular Biology-Cell Culture for Biochemists, Work and Burdon (eds.) Elsevier, Amsterdam. Additional details regarding tissue culture procedures of particular interest in the production of influenza virus in vitro include, e.g., Merten et al. (1996) *Production of influenza virus in cell cultures for vaccine preparation* in Cohen and Shafferman (eds.) Novel Strategies in Design and Production of Vaccines, which is incorporated herein in its entirety for all purposes. Additionally, variations in such procedures adapted to the present invention are readily determined through routine experimentation and will be familiar to those skilled in the art.

In a specific embodiment of the invention, host cells of the invention are cultured and/or infected under serum-free conditions, in the presence or absence of trypsin, and are cultured and/or infected at temperatures ranging from 30 degrees Celsius to 39 degrees Celsius; or 30 degrees Celsius, or 31 degrees Celsius, 32 degrees Celsius, 33 degrees Celsius, 34 degrees Celsius, 35 degrees Celsius, 36 degrees Celsius, 37 degrees Celsius, 38 degrees Celsius, or 39 degrees Celsius.

Cells for production of influenza virus can be cultured in serum-containing or serum free medium. In some cases, e.g., for the preparation of purified viruses, it is typically desirable to grow the host cells in serum free conditions. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

Regardless of the culture volume, in many desired aspects of the current invention, it is important that the cultures be maintained at an appropriate temperature, to insure efficient recovery of recombinant and/or reassortant influenza virus using temperature dependent multi plasmid systems (see, e.g., Multi-Plasmid System for the Production of Influenza Virus, cited above), heating of virus solutions for filtration, etc. Typically, a regulator, e.g., a thermostat, or other device for sensing and maintaining the temperature of the cell culture system and/or other solution, is employed to insure that the temperature is at the correct level during the appropriate period (e.g., virus replication, etc.).

In some methods (e.g., wherein reasserted viruses are to be produced from segments on vectors) vectors comprising influenza genome segments are introduced (e.g., transfected) into host cells according to methods well known in the art for introducing heterologous nucleic acids into eukaryotic cells, including, e.g., calcium phosphate co-precipitation, electroporation, microinjection, lipofection, and transfection employing polyamine transfection reagents. For example, vectors, e.g., plasmids, can be transfected into host cells, such as COS cells, 293T cells or combinations of COS or 293T cells and MDCK cells, using the polyamine transfection reagent TransIT-LT1 (Mirus) according to the manufacturer's instructions in order to produce reasserted viruses, etc. Approximately 1 μg of each vector to be introduced into the population of host cells with approximately 2 μl of TransIT-LT1 diluted in 160 μl medium, preferably serum-free medium, in a total volume of 200 μl. The DNA:transfection reagent mixtures are incubated at room temperature for 45 minutes followed by addition of 800 μl of medium. The transfection mixture is added to the host cells, and the cells are cultured as described above or via other methods well known to those skilled in the art. Accordingly, for the production of recombinant or reassortant viruses in cell culture, vectors incorporating each of the 8 genome segments, (PB2, PB1, PA, NP, M, NS, HA and NA) are mixed with approximately 20 μl TransIT-LT1 and transfected into host cells. Optionally, serum-containing medium is replaced prior to transfection with serum-free medium, e.g., Opti-MEM I, and incubated for 4-6 hours.

Alternatively, electroporation can be employed to introduce such vectors incorporating influenza genome segments into host cells. For example, plasmid vectors incorporating an influenza A or influenza B virus are favorably introduced into Vero cells using electroporation according to the following procedure. In brief, approximately $5\times10^6$ Vero cells, e.g., grown in Modified Eagle's Medium (MEM) supplemented with 10% Fetal Bovine Serum (FBS) are resuspended in 0.4 ml OptiMEM and placed in an electroporation cuvette. Twenty micrograms of DNA in a volume of up to 25 μl is added to the cells in the cuvette, which is then mixed gently by tapping. Electroporation is performed according to the manufacturer's instructions (e.g., BioRad Gene Pulser II with Capacitance Extender Plus connected) at 300 volts, 950 microFarads with a time constant of between 28-33 msec. The cells are remixed by gently tapping and, approximately 1-2 minutes following electroporation, 0.7 ml MEM with 10% FBS is added directly to the cuvette. The cells are then transferred to two wells of a standard 6 well tissue culture dish containing 2 ml MEM, 10% FBS. The cuvette is washed to recover any remaining cells and the wash suspension is divided between the two wells. Final volume is approximately 3.5 mL. The cells are then incubated under conditions permissive for viral growth, e.g., at approximately 33° C. for cold adapted strains. See, e.g., US20050158342, which is incorporated by reference herein.

Kits

To facilitate use of the methods and compositions of the invention, any of the vaccine components and/or compositions, e.g., virus in various formulations, etc., and additional components, such as, buffer, cells, culture medium, useful for packaging and infection of influenza viruses for experimental or therapeutic vaccine purposes, can be packaged in the form of a kit. Typically, the kit contains, in addition to the above components, additional materials which can include, e.g., instructions for performing the methods of the invention, packaging material, and a container.

EXAMPLE 1

Development of Liquid FluMist

A total of 19 monovalent bulk lots of virus were initiated under protocol, including four development lots (CB0006H, CB0008H, CG0017H, CB0018H and CB0019H). Lots CB0018H and CB0019H were conducted to supply material for various studies and are not discussed further in this application. Two lots (CB00180H and CB0012H) were combined after the ultra-centrifugation step to produce A/Sydney monovalent bulk CB0020H. Each lot was initiated with about 2000 eggs.

Egg handling and incubation conditions were set up similar to the process used for production of frozen FluMist, however, manual inoculation and harvesting were used due to the smaller scale, etc. The ultracentrifuge process was scaled down to smaller equipment made by the same manufacturer (Discovery 90, made by Hitachi and marketed by Sorvall/heraus), with a Model P32CT rotor having approximately 470 mL of total capacity. Clarified, stabilized virus harvest was loaded onto a 20% to 60% sucrose gradient, banded for one hour at 32,000 rpm, and eluted into 20 mL fractions. Fractions containing peak HA levels were pooled, diluted to 0.2M sucrose concentration, filtered through a 0.2 micron filter, and then transferred into 250 mL flexible polymer bags (Stedim) which were frozen and held below −60° C. for further manufacture.

After a short series of test runs, cGMP manufacturing was initiated to support further clinical testing of liquid FluMist. A/Beijing/262/95 (H1N1) and A/Sydney/05/97 (H3N2) were again manufactured, and the B strain was changed to B/Yamanashi/166/98. Monovalent bulks produced were frozen and shipped for blending, filing, and packaging. Of course, it will be appreciated here and throughout, that use of particular strains (e.g., Beijing, etc.) should not necessarily be taken as limiting unless specifically stated to be so. Thus for example, the methods and formulations herein can optionally use different strains each influenza season to produce different RTS compositions, etc.

Development and Clinical Trials

The process for liquid compositions was developed and included monovalent bulk lots CAZ001-024 and CAZ035-043. The clinical trial material (CTM) included monovalent bulk lots CAZ025-CAZ034.

The liquid FluMist manufacturing process developed and used for CTM-1 is divided into six discrete process stages below. The process stages 1 through 5 were defined to match the major process steps as conducted using separate manufacturing instruction documents. Stage 6 includes the entire blend and fill process. It will be appreciated that such stages can be roughly compared to the generalized steps outlined below for manufacturing/production of vaccine compositions in general.

Stages

Figure 2:
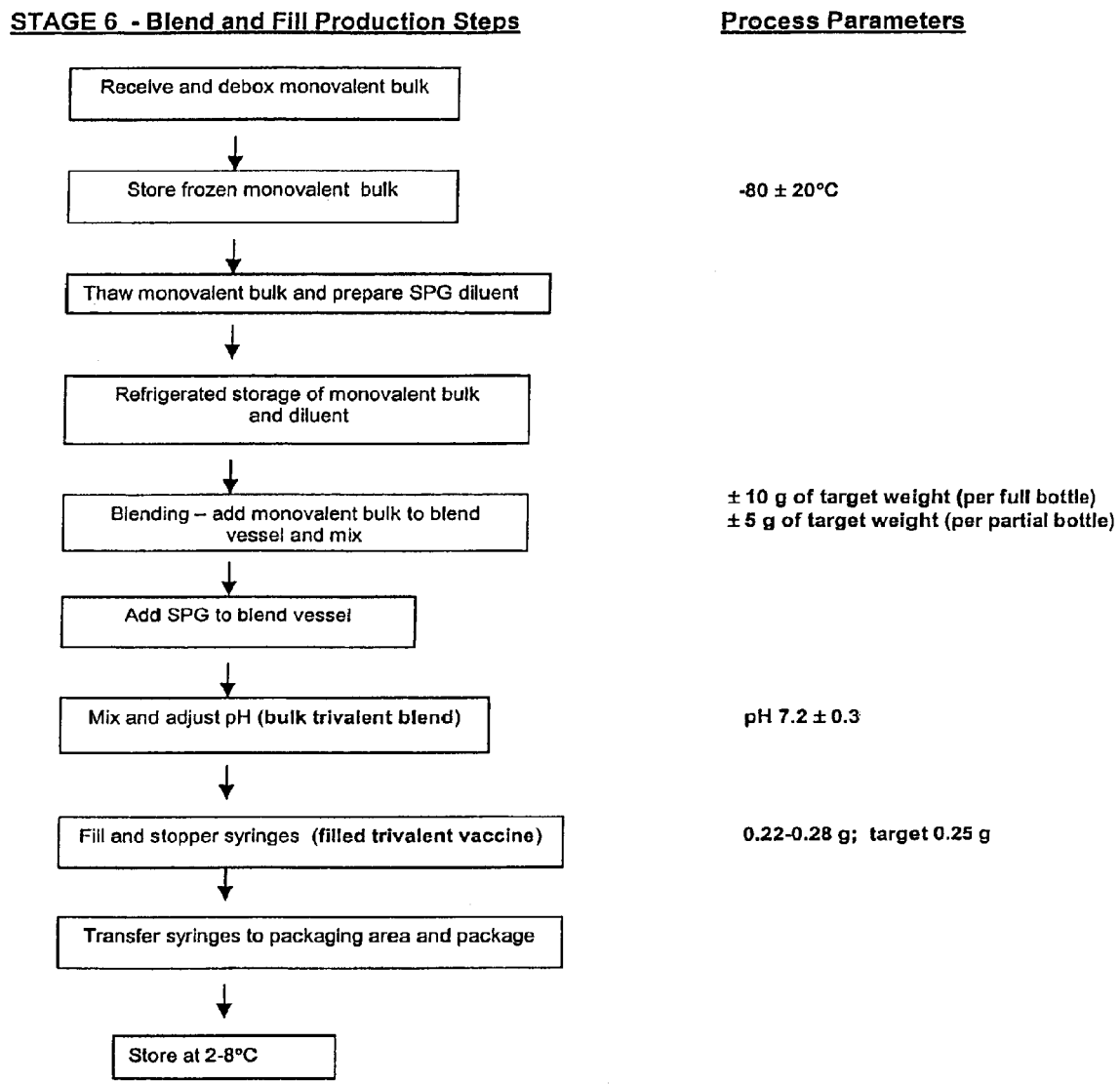
FIG. 2: Displays a flow chart illustrating a CTM Process Flow.

Stage 1: receipt and sanitization of SPF eggs; Stage 2: production of virus harvest; Stage 3: concentration of virus by zonal centrifugation; Stage 4: pooling and dilution of peak fractions; Stage 5: sterile filtration and monovalent bulk storage; and, Stage 6: blend and fill A process flow diagram for the CTM-1 monovalent bulk production is shown in FIG. 1. The blend and fill process flow is shown in FIG. 2.

Receipt and Sanitization of SPF Eggs

Specific pathogen-free (SPF) embryonated eggs were purchased from SPAFAS, Inc. which utilizes flock management and surveillance programs designed to provide suitable assurance of disease-free eggs. Eggs were laid in the United States and sanitized using Chlorwash and Quat 800 sprays. The eggs were then transported by air and road using packaging sufficient to maintain cleanliness and avoid freezing or overheating. Upon receipt, the cold fertile eggs were inspected and stored in an SPF incubation unit at 14° C.+/−2° C. with 60-80% relative humidity (RH) for a maximum of 7 days. The eggs were transferred to trays from the cartons supplied by the vendor and a batch number assigned. Eggs were placed on 36-egg Jamesway trays and the eggshell surfaces sanitized with Chlorwash and Quat 800 in an automated egg sanitization system to minimize bioburden prior to placing them in the incubator. Chlorwash was prepared at a range of 43-44° C. and 48-49° C. and Quat 800 was prepared at a range of 48-49° C. Following sanitization, the eggs were placed on trolleys and air dried at ambient temperature for not less than 2 hours. The eggs were then placed in a Buckeye Incubator and incubated at 37.5° C.+/−1° C. with 60-80% RH for 264 hours+/−12 hours. After incubation, the SPF eggs were transferred from the SPF egg unit to a candling area. Using a fiber optic lamp, the position of the air sac was located in each egg. Dead or infertile eggs were discarded, and the fertile eggs marked for inoculation.

Production of Virus Harvests

The fertile eggs were surface sanitized with 70% industrial methylated spirits (IMS) prior to inoculation and then transferred for mass inoculation. In preparation of the diluted manufacturer's working virus seed (MWVS), the master virus seeds used to produce the MWVS for phase 1 clinical trials were produced using the classical reassortment method. The MWVS, was transferred into the AVU and serial dilutions of the thawed MWVS were prepared in sterile 0.01M phosphate buffered saline, pH 7.7 within a microbiological safety cabinet using a sterile disposable pipette for each transfer. The inoculation occurred under laminar flow in a class 10,000 room using a semi-automatic Bibby inoculation machine, which penetrates and inoculates 36 eggs per tray. The target titer of the inoculum was $\log_{10} 2.1$ TCID$_{50}$ per 0.1 mL and the dilution was calculated from the predetermined titer of the MWVS. Preparation of each virus inoculum was completed within 2 hours of the removal of the vial from the freezer. Aliquots of the inoculum were stored at 5+/−3° C. until use. Inoculum was used within 8 hours of preparation.

Inoculation of SPF Eggs

Each tray of eggs was hand-fed into the Bibby automated inoculation machine. A punch was used to pierce the eggshell and penetrate the egg to a preset adjustable depth. The inoculation needles extended into the egg and the dosing pump delivered 0.1 mL of the MWVS inoculum into each egg after which the punch was withdrawn. Following inoculation, the egg tray was removed by an operator and the process repeated with a new tray of eggs. The CAIV inoculated eggs were incubated at 33+/−1° C. for a time determined by the growth curve of the virus strain. After incubation, the SPF embryonated eggs were chilled to 28° C. for 18+/−6 hours. At the end of chilling, the eggs were transferred for the harvesting step.

Concentration of Virus by Zonal Centrifugation

Virus Harvest (VH)

Eggs were harvested with an automatic harvest machine (Bibby). The trays were hand fed to a decapitation station where the upper section of the eggshell was removed to create an access hole for harvest needle entry. The eggs were visually inspected prior to harvest and unsuitable eggs (e.g., discolored) rejected. The acceptable eggs proceeded to a harvest station, where the allantoic fluid was withdrawn using needles and suction provided by a vacuum system. The harvest was collected mixed in a 100 L jacketed stainless vessel with a jacket temperature of 2-8° C. Samples of the virus harvest were collected from the VH pool and tested for: potency (TCID$_{50}$), safety, avian leucosis, *M. tuberculosis*, mycoplasma, extraneous virus, identity, reverse transcriptase assay, virus genotype, virus phenotype, and attenuation.

Stabilization and Clarification

The pooled virus harvest (VH) was immediately stabilized at 2-8° C. to a final concentration of 0.2 M sucrose, 0.01M phosphate, 0.005M glutamate (SPG), with 10×SPG (9 parts VH to 1 part 10×SPG). Samples were collected for potency and bioburden prior to clarification. The stabilized virus harvest was clarified by 5 μm depth filtration to remove particulates prior to purification by high-speed continuous flow centrifugation. Clarified virus harvest was sampled for potency.

Zonal Centrifugation, Collection, and HA Assay of Peak Fractions

Prior to use, the centrifuge rotor was sanitized with a 1:20 dilution of concentrated formaldehyde solution. The clarified VH was loaded onto a sucrose gradient (10-60% sucrose in phosphate buffer, pH 7.2) for continuous high-speed centrifugation using a Hitachi CP40Y zonal centrifuge. The gradient was formed by addition to the centrifuge of a 60% sucrose solution followed by a 10% sucrose solution in phosphate buffer. The centrifuge speed was set to 4,000 rpm for 20 minutes to allow the sucrose solutions to form a density gradient. Centrifuge temperature was set at 2-8° C. during gradient formation. Following gradient formation, buffer flow was initiated and the rotor speed was increased to 40,000 rpm, before the clarified VH was loaded onto the gradient at a rate of 20 L per hour at 40,000 rpm. For a typical CTM-1 batch with 10,000 eggs harvested and 6 mL/egg, the duration of the loading step was about three hours. Following loading of the clarified VH, centrifugation was continued at 40,000 rpm for an additional hour to allow the virus to band. The virus particles migrated to the 38-45% sucrose portion of the gradient and concentrate into a "band." At the end of this step, the centrifuge was gradually slowed and then stopped to allow collection of the virus peaks. 100 mL fractions were collected under laminar flow into 125 mL sterile polycarbonate bottles. Fractions were held at 2-8° C. for approximately 1 hour while fractions were assayed for HA activity. Peak fractions were typically found between 38-45% of the sucrose gradient.

Pooling and Dilution of Peak Fractions

The centrifuge peak fractions, as identified by the HA assay, were pooled under a laminar flow hood by aseptically pouring the fractions into a 5 L sterile glass bottle, and mixed by swirling. The refractive index (RI) was read to determine sucrose concentration and the pool sampled for potency. The centrifuge peak fraction pool (CP) was diluted by aseptically adding a calculated volume of sterile cold (2-8° C.) phosphate-glutamate buffer, pH 7.2 (PBG buffer) to a final concentration of 0.2M sucrose, 0.1M phosphate, and 0.005 M glutamate. This was typically a 1:6 dilution. The diluted centrifuge peak fraction pool (DCP) was sampled for potency and bioburden.

Sterile Filtration and Monovalent Bulk Storage

The DCP was pumped through sterile tubing to a Class 100 filling room for sterile filtration. The DCP was sterile filtered with a 0.22 μm filter into a sterile 5 L glass bottle under a Laminair Air Flow hood. The filtered monovalent bulk was mixed and sampled for potency, identity, and sterility testing. The 0.22 μM filter was integrity tested before and after the filtration process. The MB was then aliquoted into sterile one liter polycarbonate bottles. The MB was collected in 500 mL aliquots with a total volume of three to four liters. The sterile one-liter PC bottles were stored at −60° C. or below. The titer of the bulk virus was determined by $TCID_{50}$ assay. Monovalent bulk was then shipped at ≦−60° C. for blending and testing.

Blend and Fill

The major steps for the blend and fill process of the preparation of the bulk trivalent blend were: Thawing, Preparation of Diluent, Blending, Filling, and Packaging.

Thawing and Blending

The appropriate 1 bottles of monovalent bulk were removed from frozen storage (≦−60° C. for MB) and transferred to a thaw room. The required quantities of the three individual monovalent bulks and SPG diluent were calculated based on the bulk infectivity titer and the required formulation strength. The bottles of MB were loaded into a 33±3° C. water bath and manually agitated every five minutes. Thawing was monitored visually to ensure that all bottles were thawed before leaving the water bath, and that all thawed bottles were removed every 15 minutes. Once thawed, the bottles of MB were moved to a 5±3° C. refrigerator and held until all of the required bottles had been thawed.

Sterile sucrose phosphate glutamate (SPG) diluent was manufactured by BioWhittaker (Walkersville, Md.). Just prior to manufacture of the liquid FluMist blend, about one-third of the amount of SPG diluent required for the blend was added to a sterile 2-L bottle. The bottle was warmed to room temperature, then hydrolyzed porcine gelatin (powder) was added in the amount need to reach a level of 10 mg/ml in the final blend. The SPG diluent was then passed through the filter (washing through any residual gelatin) to reach the target volume specified in the blend calculation and stored at 5±3° C. until use.

Thawed bottles were moved to a blend room and virus aseptically transferred to a 5 L glass process vessel. The vessel was kept at 5±3° C. throughout the blending process and the subsequent filling process by using refrigerated cold packs. The SPG-gelatin diluent was added after the three virus strains had been added, and, if necessary, the pH was adjusted with HCl to 7.2±0.3. The three virus strains and diluent were blended by continuous mixing with a magnetic stir bar and stir plate.

Filling and Packaging

Following pH adjustment, the bulk trivalent blend vessel was moved to a filling room and connected to an INOVA filler. The INOVA filling machine filled a preset volume of product into a row of eight BD HYPAK disposable sprayers and then stoppered the sprayers. Sprayer filling and stoppering operations and weight check verifications continued as directed. A new tub of sprayers was manually placed at the in-feed stations upon completion of each fill cycle and the tub of filled sprayers removed to the discharge station. The blend vessel was maintained at 5±3° C. with cold packs during the filling process.

Following filling of the nasal sprayers, the filled trivalent vaccines were loaded into tubs and immediately transported via cart to a packaging area for final packaging and labeling. Packaged and labeled sprayers were stored at 5±3° C.

Optimization of Upstream Operating Parameters

Clarification of Harvest by Filtration (5 μm)

Filtration vs. Low Speed Centrifugation: Clarification potency losses using the standard low-speed centrifugation for frozen FluMist are typically estimated at 0.2 to 0.3 $\log_{10}$ $TCID_{50}$/mL. An estimated centrifugation loss for two strains was: titer loss was negligible for one strain and 0.3 logs (59% step yield) for a second strain using the standard conditions of 3400 g for 20 minutes. When a 5 micron depth filter was used as an alternative to centrifugation during pre-CTM development runs, the average clarification step yield was estimated at 41%. When $TCID_{50}$ assay variability was taken into consideration, it was concluded that either method of clarification provided better results than adding after clarification. Filtration was chosen as the clarification method based on ease of operation and scalability.

Comparison of Depth Filter Pore Sizes: Development lots CAZ015-CAZ017 plus the ten CTM-1 lots CAZ025 through CAZ034 were used to estimate depth filtration losses using the CTM-1 process. A/Beijing, A/Sydney, and B/Harbin have clarification step yields of 147%, 78%, and 73% respectively for the 5 μm clarification step.

The 5 μm (Pall Profile II) filter was compared to a 20 μm depth filter (Pall Profile Star), which was used for lots CAZ035 (A/Sydney), CAZ036 (A/Beijing) and CAZ037 (B/Harbin). A/Beijing, A/Sydney, and B/Harbin had clarification step yields of 65%, 35%, and 209% respectively for the 20 μm clarification step. These yields were comparable to 5 μm clarification results, however a process change to the 20 μm filter was not recommended for all embodiments due to significant contamination of clarified harvests by red blood cells when larger pore size was used.

Optimization of Downstream Operating Parameters:

Centrifuge Scale

Centrifuge loading and temperature studies were performed using the large-scale CP40Y centrifuge and RP40CT Type D continuous-flow rotor; these compared various egg batch sizes and centrifuge temperature set points (see FIG. 3). CAZ 015 (B/Harbin), CAZ018 (A/Sydney), CAZ020 (A/Beijing) and CAZ022 (A/Sydney) had batch sizes of 10K eggs and a centrifuge set temperature of 4° C. CAZ 016 (B/Harbin), CAZ019 (A/Sydney), and CAZ021 (A/Beijing) had batch sizes of 20K eggs and a centrifuge set temperature of 14° C. A loading flow rate of 20 L/hr was used for all of these studies. Percent recovery in the diluted peak-fraction pool (step yield) was based on the clarified harvest titer in the figure. As can be seen, lots with 10K egg batches had a recovery range from 40-184% whereas the 20K egg batches ranged from 40-55%. The average recovery for the 10K batch size was 113% and the 20K egg batch recoveries averaged 46%. A batch size of 10,000 eggs per run was selected for CTM manufacturing as a conservative limit in this step of the development process.

Temperature

Development runs CAZ015 through CAZ022 were performed using ultracentrifuge rotor set point temperature either at 4° C. or 14° C. With one exception, the development runs at 14° C. were also run at larger scale than typical (20,000 eggs per batch). In general these batches had lower recoveries of live virus, however this could be due to centrifuge loading rather that temperature effects. In view of the better results at 4° C. and the possibility of increased microbial growth rates at higher temperatures, a temperature of 4° C. was selected as the ultracentrifuge temperature set point at this point in the development of the process.

Clinical Trial 1 (CTM-1)

The monovalent virus lots for CTM-1 were produced and included monovalent bulk lots CAZ025 through CAZ034. In-process QC assay results for the CTM-1 monovalent bulk lots are presented in FIG. 3 and herein. Average step yields per strain are presented in FIG. 3 and herein. Results are summarized below.

Potency: The potencies ($\log_{10}TCID_{50}$ mL) of B/Harbin and A/Beijing virus harvest lots were equal or greater than 8.1. A/Sydney ranged from 7.5 to 8.8 except for CAZ030, which showed very low titer (6.0) because of yolk contamination in the harvest. The titer of the monovalent bulk for A/Beijing was 9.3 or above, for B/Harbin the titer ranged from 8.4 to 9.85 and for A/Sydney ranged from 7.9 to 8.6 (excluding CAZ030). For CAZ030 the titer was below the acceptable level for blending as discussed below.

Process Yield: Process yields for each lot are referenced in the Figures and discussed further herein. Process yields were not corrected for sampling losses. A/Beijing had an average overall process yield of 16% (163 doses/egg), A/Sydney had an average yield of 13% (6 doses/egg), and B/Harbin had an average yield of 93% (86 doses/egg). See figures. The erratic yield estimates reflect assay variability as well as the actual process performance. In particular, the B/Harbin results were skewed upward by a very high estimate of Lot CAZ028 monovalent bulk titer (resulting in estimated 252% process yield and 246 doses/egg). The diluted peak pool titer in this case was determined at 0.95 logs higher than the centrifuge peak pool, though a decline would be expected due to dilution. Likewise the filtered monovalent bulk titer was higher than the prefiltered material, which can be accounted for by assay variability. The other two B/Harbin lots, (CAZ026 and CAZ027) had process yields of 20% and 8% respectively, and an egg yield of 7 doses/egg for both lots. The trivalent blends that included bulk lot CAZ028 (CBF1004 and CBF1007) resulted in B/Harbin potencies in final product sprayers that were 0.6 and 0.4 $\log_{10}$ $TCID_{50}$ per dose. This further suggests that the CAZ028 monovalent bulk titer was overestimated.

Bioburden and Endotoxin: Virus harvest, stabilized harvest and diluted centrifuge peak fractions were tested for bioburden. Bioburden test results do not give a clear picture of organism loads through the process: test results on virus harvest and diluted centrifuge peak fraction pool samples consisted primarily of "none detected" (eight readings); or ">100 cfu/mL" (ten readings) with only two intermediate values. Endotoxin values for the monovalent bulks varied from <5 EU/mL to 587 EU/mL.

Sucrose Concentration: The centrifuge peak fraction pools had sucrose concentrations ranging from 39 to 43.5% (CAZ030 was not included in the range). The monovalent bulks had an average sucrose concentration of 7.6%.

The monovalent bulk release assay results are presented in the figures. All of the CTM-1 lots except for CAZ030 (which was not tested) passed the bulk release assays.

SDS-PAGE Analysis: Monovalent bulks were further characterized by 10% SDS-PAGE gels stained with Gel Code Blue. Based on the calculated protein molecular weights and number of copies per particle for influenza A and B strains, gel bands in the region of 50-60 kDa (HA1 protein), 56 kDa (NP protein) and 27 kDa (M1 protein) would be expected to be prominent in gels of purified influenza virus. Ha2 protein (23 to 30 kD) may also be present.

SDS-PAGE gels for A/Beijing/262/95 CAZ031, and 33 and A/Sydney/05/97 CAZ029, 30, and 34 were compared. The range of resolution for the 10% gels was nominally 200-31 kDa. Because of this limitation, interpretation of HA1 protein (23-30 kDa) and M protein bands (21-27 kDA) should be made with caution.

For A/Beijing and A/Sydney monovalent bulk (MB) lots, a dark band was observed in the expected region of NP protein (just above the 55 kDa marker) for the A/Beijing samples, and a band was seen just above 116 kDa for both strains. Both strains contained a band near the gel front (below 31 kD) consistent with M protein. The HA1 band expected at or just above the 66 kD marker was less strong, possibly due to heterogeneity in glycoprotein molecular weight resulting in a more dispersed banding pattern. Staining of the putative NP1 protein also seems to be diminished. For the A/Sydney samples a wider variety of bands were observed, consistent with a greater proportion of egg protein in the monovalent bulk.

Doses per Lot and Egg: The dose calculation for all three strains was based on a 0.24 mL average fill volume containing 1.2E+07 $TCID_{50}$ particles. Based on the dose calculation above, the A/Beijing monovalent lots had an average of 1,576, 022 total doses per lot. Average total doses per lot for B/Harbin and A/Sydney were 601,446 and 50,825 doses per lot respectively, or 38% and 3.2% of the average A/Beijing total doses per lot respectively. These results translate to the following values for monovalent doses per egg: 163 doses/egg for A/Beijing, 86 doses/egg for B/Harbin-like and 6 doses/egg for A/Sydney. The calculation for doses/egg was based on the total number of eggs harvested to manufacture the lot.

Summary of Egg Yields: A/Sydney had the highest average harvest volume per egg yield, followed by A/Beijing and B/Harbin. The yield per egg averaged 5.6 mL/egg for B/Harbin, 6.5 mL/egg for A/Beijing, and 6.8 mL/egg for A/Sydney. The overall yield of viable eggs for production averaged 82%. Egg yields were based on the total number of eggs harvested compared to total number of eggs for production. Percent eggs rejected pre-inoculation averaged 10%. Percent rejection post-incubation averaged 5%, with the exception of CAZ028, which had a 29% rejection rate.

Purification Yield Summary ($TCID_{50}$): Clarified harvest potency values were higher than the starting material for some of the lots, resulting in step yields greater than 100%. Step yield estimates are affected by the variability of the $TCID_{50}$ assay, which had a standard deviation above $0.3 \log_{10} TCID_{50}$/mL as performed at the time of the production runs. In addition, the step yield at the Diluted Centrifuge Pak Fraction Pool step varies widely for all three strains and is greater than 100% for all ten CTM lots. This appears to be due to a systematic downward bias of titers for Centrifuge Peak Fraction Pools (as suggested by the >100 yield of the next step), thought to be related to the high sucrose levels in these samples.

Comments on CTM-1 Lots

In the various embodiments and example herein it is preferable that no yolk contamination take place of the harvest fluids which could occur, e.g., with improper harvest machine settings.

0.2 micron filtration step: The batch record in effect specified a Pall Kleenpak disposable filter, however this was not used for any CTM lots. Lots CAZ025-030 used a cartridge filter (AB1DFL7PH4—Pall hydrophilic PVDF Fluorodyne II filter) with housing instead of the Kleenpak. The filters had similar materials of construction (hydrophilic PVDF), however the filter areas were 5100 cm$^2$ for the Fluorodyne II cartridge filter vs. 1500 cm$^2$ for the Kleenpak Fluorodyne II filter. For lots CAZ031/032/033/034 a disposable Pall Nova-Sip C3DFLP1 filter assembly was used instead of the Kleenpak. The membrane surface area for the C3DFLP1 filter was the same as the Kleenpak filter (1500 cm$^2$).

Temperature excursions: During the second incubation step for CAZ031, the temperature rose to 34.4° C. for 13 hours and for CAZ032 the temperature dropped to 31.5° C. for 4 hours. These lots reached normal harvest titers above 9.0 log 10 TCID50/mL, so the excursions were not regarded as having impacted the product.

Summary

Based on two Clinical Trial Manufacturing Campaigns (CTM-1 and CTM-2), the liquid FluMist process development and manufacturing work indicates that the process is suitable to produce clinical supplies that pass release specifications. Aggregate data from both CTM runs and various development studies leads to the following estimates of median process yield:

Clarification: 50% yield
Ultracentrifuge purification: 50% yield
Peak dilution and sterile filtration: 20 to 50% yield

EXAMPLE 2

Stability Testing

A trivalent vaccine formulation was prepared comprising three different reassortant influenza viruses (7.0+/−0.5 log 10 FFU/dose [approximately 7.0+/−0.5 $\log_{10}$ $TCID_{50}$/dose]) and comprising 200 mM sucrose; 1% (w/v) porcine gelatin hydrolysate; 1.21% (w/v) arginine monohydrochloride [equivalent to 1% (w/v) arginine base]; and 5 mM monosodium glutamate in 100 mM potassium phosphate buffer (pH 7.2). The stability of the formulation was stored at −25.0 degrees C+/−5.0 degrees for greater than or equal to 24 hours, but less than or equal to two weeks and then stored at 2-8 degrees C. for various time periods. This formulation (e.g., lot 0141500003) was determined to be stable for at least 12 weeks at 4-8 degree C. In particular, the potency for each strain of virus remained within 0.5 log 10 of the beginning potency prior to 4-8 degree C. storage.

Other studies have shown that equivalent formulations (comprising three different reassortant influenza viruses (7.0+/−0.5 log 10 FFU/dose [approximately 7.0+/−0.5 log 10 $TCID_{50}$/dose]) and comprising 200 mM sucrose; 1% (w/v) porcine gelatin hydrolysate; 1.21% (w/v) arginine monohydrochloride [equivalent to 1% (w/v) arginine base]; and 5 mM monosodium glutamate in 100 mM potassium phosphate buffer, pH 7.2) of different clinical lots (e.g., "Campaign 3") are stable for about 12-15 months at 5.0 (+/−3.0) degrees C.

Subsequent studies have shown that formulations comprising only 200 mM sucrose; 1% (w/v) gelatin hydrolysate; 1.21% (w/v) arginine monohydrochloride [equivalent to 1% (w/v) arginine base] in 100 mM potassium phosphate buffer, pH 7.2, but without glutamate, had equivalent stability as the above formulations with glutamate.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method for making a refrigerator-stable live cold-adapted influenza virus composition, comprising:
   (a) clarifying a viral harvest comprising live cold-adapted influenza viruses by filtration, thereby producing a clarified viral harvest filtrate;
   (b) subjecting the clarified viral harvest filtrate to continuous zonal centrifugation, thereby producing a further clarified viral harvest;
   (c) sterilizing by sterile filtration the further clarified viral harvest, thereby producing a sterilized viral harvest; and
   (d) combining the sterilized viral harvest with components of a stabilizer consisting of:
      (i) 2% to 8% sucrose weight/volume (w/v), 0.75% to 2% arginine w/v, 0.02% to 0.15% glutamate w/v, 0.05% to 2% gelatin hydrolysate, and a buffer, or
      (ii) 2% to 8% sucrose w/v, 0.75% to 2% arginine w/v, 0.05% to 2% gelatin hydrolysate, and a buffer;
   thereby producing a refrigerator-stable live cold-adapted influenza virus composition, wherein each amount of each of the components of the stabilizer is the final amount in the virus composition, and which virus composition exhibits a potency loss of less than 1.0 log over a 12 month period when stored at 4° C. to 8° C.

2. The method of claim 1, wherein the cold adapted influenza viruses comprise one or more of: an attenuated cold adapted influenza virus, a temperature-sensitive cold adapted influenza virus, or an attenuated cold-adapted temperature-sensitive influenza viruses.

3. The method of claim 1, wherein the cold adapted influenza viruses comprise a genetic backbone of one or more of the following influenza viruses: A/Ann Arbor/6/60 and B/Ann Arbor/1/66.

4. The method of claim 1, wherein the viral harvest is stabilized at 2° C. to 8° C. by the addition of another stabilizer prior to clarification in (a).

5. The method of claim 4, wherein the other stabilizer comprises sucrose, phosphate and glutamate (SPG).

6. The method of claim 5, wherein the other stabilizer is added to a final concentration of 0.2 M sucrose, 0.01 M phosphate and 0.005 M glutamate.

7. The method of claim 1, wherein the viral harvest is clarified in (a) through a filter ranging from 0.2 microns to 1.5 microns.

8. The method of claim 7, wherein the viral harvest is clarified in (a) by filtration through a filter ranging from 0.2 microns to 0.8 microns.

9. The method of claim 1, wherein the viral harvest is clarified by filtration through a 5 micron filter in (a).

10. The method of claim 1, wherein the viral harvest is clarified by depth filtration through one or more filters in (a).

11. The method of claim 10, wherein the viral harvest is clarified in (a) through two or more filters.

12. The method of claim 10, wherein the viral harvest is clarified in (a) by depth filtration through a filter ranging from 0.2 microns to 0.8 microns.

13. The method of claim 1, wherein the continuous zonal centrifugation in (b) is performed over a sucrose density gradient.

14. The method of claim 13, wherein the sucrose density gradient is a 10% to 60% sucrose gradient in phosphate buffer.

15. The method of claim 14, wherein the sucrose gradient in phosphate buffer is at pH 7.2.

16. The method of claim 1, wherein the continuous zonal centrifugation in (b) is performed at a temperature of 2° C. to 8° C.

17. The method of claim 16, wherein the continuous zonal centrifugation is performed at a temperature of 4° C.

18. The method of claim 1, which further comprises adding to the further clarified viral harvest in (c) a diluent comprising phosphate and glutamate.

19. The method of claim 18, wherein the diluent is added to the further clarified viral harvest prior to the sterilizing in (c).

20. The method of claim 18, wherein the diluent is added to the further clarified viral harvest to a final concentration of 0.2 M sucrose, 0.1 M phosphate and 0.005 M glutamate.

21. The method of claim 1, which further comprises in (c) blending the sterilized viral harvest with at least one other sterilized viral harvest.

22. The method of claim 21, wherein the sterilized viral harvest is blended with two other sterilized viral harvests.

* * * * *